United States Patent
Duggan

(10) Patent No.: US 8,916,523 B2
(45) Date of Patent: *Dec. 23, 2014

(54) VIP FRAGMENTS AND METHODS OF USE

(71) Applicant: Vectus Biosystems Limited, Rosebery, New South Wales (AU)

(72) Inventor: Karen Annette Duggan, Randwick (AU)

(73) Assignee: Vectus Biosystems Limited, Rosebery, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/903,227

(22) Filed: May 28, 2013

(65) Prior Publication Data

US 2013/0244934 A1    Sep. 19, 2013

Related U.S. Application Data

(62) Division of application No. 12/096,768, filed as application No. PCT/AU2006/001869 on Dec. 8, 2006, now Pat. No. 8,470,778.

(30) Foreign Application Priority Data

Dec. 9, 2005 (AU) .................. 2005906947

(51) Int. Cl.

| A61K 38/08 | (2006.01) |
|---|---|
| A61K 38/10 | (2006.01) |
| C07K 7/06 | (2006.01) |
| A61K 45/06 | (2006.01) |
| A61K 38/22 | (2006.01) |
| C07K 7/08 | (2006.01) |
| C07K 14/575 | (2006.01) |
| A61K 38/00 | (2006.01) |

(52) U.S. Cl.
CPC ... *C07K 7/08* (2013.01); *C07K 7/06* (2013.01); *A61K 45/06* (2013.01); *A61K 38/08* (2013.01); *A61K 38/2278* (2013.01); *A61K 38/00* (2013.01); *A61K 38/10* (2013.01); *C07K 14/57563* (2013.01)
USPC ................. 514/13.1; 514/15.7; 514/16.4

(58) Field of Classification Search
None
See application file for complete search history.

(56) References Cited

U.S. PATENT DOCUMENTS

| 5,972,883 A | 10/1999 | Gozes et al. |
| 7,951,777 B2 | 5/2011 | Duggan |

(Continued)

FOREIGN PATENT DOCUMENTS

| GB | 2196634 A | 5/1988 |
| WO | 0243746 A2 | 6/2002 |
| WO | 2005120545 A1 | 12/2005 |

OTHER PUBLICATIONS

Bodanszky et al. Synthesis and Pharmacological Properties of the N-terminal Decapeptide of the Vasoactive Intestinal Peptide (VIP). 1977, Journal of Medicinal Chemistry, vol. 20, No. 11, pp. 1461-1464.*

(Continued)

*Primary Examiner* — Jeffrey E Russel
(74) *Attorney, Agent, or Firm* — Polsinelli PC; Teddy C. Scott, Jr.; Ron Galant

(57) ABSTRACT

The invention relates to composition comprising a pharmaceutically effective amount of one or more functional vasoactive intestinal peptide (VIP) fragments, and the use of those compositions in the treatment of fibrosis, hypertension and other disorder.

13 Claims, 9 Drawing Sheets

(56) References Cited

U.S. PATENT DOCUMENTS 8,470,778 B2 * 6/2013 Duggan .................. 514/13.1
2009/0005315 A1 1/2009 Duggan

OTHER PUBLICATIONS

Diez, et al. Clinical aspects of hypertensive myocardial fibrosis. Current Opinion in Cardiology. 2001, vol. 16, pp. 328-335.

Fournier, et al. Synthesis, Conformational Studies and Biological Activities of VIP and Related Fragments. Peptides. 1984, vol. 5, pp. 169-177.

Gourlet, et al. Analogues of VIP, Helodermin, and PACAP Discriminate between Rat and Human VIP1 and VIP2 Receptors. Annals New York Academy of Sciences. 1998, vol. 865, pp. 247-252.

Onoue, et al. Structure-activity relationship of synthetic truncated analogues of vasoactive intestinal peptide. Life Sciences. 2004, vol. 74, pp. 1465-1477.

Summers, et al. A Lymphocyte-Generated Fragment of Vasoactive Intestinal Peptide. The Journal of Pharmacology and Experimental Therapeutics. 2003, vol. 306, No. 2, pp. 638-645.

Varagic et al. Heart, aging, and hypertension. Current Opinion in Cardiology. 2001, vol. 16, pp. 336-341.

Nagano, et al. The Relaxation Effects of VIP and its C-terminal Deleted Peptides on Mouse Stomach. Peptide Science 2001, pp. 147-150.

* cited by examiner

Systolic blood pressure (SBP) after 4 weeks treatment in SHR on 2.2% salt diet. Peptides were infused at 5pmol/kg/min

US 8,916,523 B2

VIP FRAGMENTS AND METHODS OF USE

REFERENCE TO THE SEQUENCE LISTING

Applicant hereby makes reference to the sequence listing, which is contained in a file named "020001USPCsequencelisting.TXT" (18.3 Kb, created Oct. 16, 2011) and is hereby incorporated by reference.

TECHNICAL FIELD

This invention relates to compositions and methods for therapeutic or prophylactic treatment of myocardial fibrosis or associated conditions. In particular this invention concerns compositions comprising certain active fragments of VIP and their use in the treatment of myocardial fibrosis.

BACKGROUND

Any discussion of the prior art throughout the specification should in no way be considered as an admission that such prior art is widely known or forms part of common general knowledge in the field.

In myocardial fibrosis, heart muscle is replaced by fibrous or scar tissue. This can interfere with the flexibility of the heart muscle. It can lead to a decrease in function and, eventually, to overt heart failure. Use of VIP and certain fragments of VIP in therapeutic and prophylactic treatment of myocardial fibrosis and related conditions was described in PCT/AU2005/000835, incorporated in its entirety herein by reference.

Conventional view of structure/function relationship with respect to VIP activity is that the N-terminal amino acid residues (1-5) are important and necessary for signal delivery once VIP binds to its receptor. Further, there are certain key amino acid residues throughout the VIP molecule, distal to the N-terminus, that are important for receptor binding. This would suggest that fragments of VIP lacking either the N-terminal residues or significant portions that encompass the receptor binding residues would not be fully functional. Earlier studies with two VIP fragments, described in PCT/AU2005/000835, indicate that such fragments of VIP could be active, at least in the treatment of myocardial fibrosis.

It is an object of the present invention to identify additional fragments of VIP that are active in the treatment of conditions such as myocardial fibrosis, that would overcome certain disadvantages associated with using the entire VIP molecule or large portions thereof, or at least provide a useful alternative.

SUMMARY OF THE INVENTION

Despite the currently prevailing view, it was surprisingly found that activity of VIP and its fragments in the treatment and/or prevention of myocardial fibrosis is not curtailed by either deletion of the N-terminal residues of VIP or the majority of amino acid residues responsible for receptor binding.

In a broad aspect, the invention relates to compositions for prophylactic or therapeutic treatment of myocardial fibrosis or an associated condition, such as hypertension, comprising a pharmaceutically effective amount of one or more functional vasoactive intestinal peptide (VIP) fragments. Most preferably, the (VIP) fragments have as a core sequence amino acid residues 6 to 10 of native VIP (SEQ ID NO: 1), or conservative substitutions thereof. However, they may also have as a core sequence amino acid residues 16 to 25 of native VIP (SEQ ID NO: 1), or conservative substitutions thereof.

Accordingly, in a first aspect the invention provides a composition for prophylactic or therapeutic treatment of myocardial fibrosis or an associated condition, the composition comprising a pharmaceutically effective amount of one or more functional vasoactive intestinal peptide (VIP) fragments having as a core sequence amino acid residues 6 to 10 of native VIP (SEQ ID NO: 1), or conservative substitutions thereof.

The preferred active fragments of VIP are VIP(4-16) (SEQ ID NO: 35), VIP(6-16) (SEQ ID NO: 72), VIP(6-10) (SEQ ID NO: 66), VIP(6-12) (SEQ ID NO: 68), VIP(6-20) (SEQ ID NO: 76) and VIP(6-24) (SEQ ID NO: 80), with the proviso that fragments VIP (1-12) (SEQ ID NO: 91) and VIP (6-28) (SEQ ID NO: 84) are not included. However, the use of VIP fragments, including VIP (1-12) (SEQ ID NO: 91) and VIP (6-28) (SEQ ID NO: 84) for the treatment of myocardial fibrosis and other associated conditions such as hypertension are encompassed by the present invention The pharmaceutically effective amount of an active VIP fragment will vary according to the patient and/or with the severity of the disease or condition. These variables can be ascertained by one skilled in the art by routine experimentation. An appropriate dosage range, as a starting point, can be derived from dosages administered in the animal models described herein, or with reference to PCT/AU2005/000835.

Accordingly, in a second aspect the invention provides a composition for prophylactic or therapeutic treatment of myocardial fibrosis or an associated condition, the composition comprising a pharmaceutically effective amount of one or more functional vasoactive intestinal peptide (VIP) fragments having as a core sequence amino acid residues 16 to 25 of native VIP (SEQ ID NO: 1), or conservative substitutions thereof.

Accordingly, in a third aspect the invention provides a composition for prophylactic or therapeutic treatment of myocardial fibrosis or an associated condition, the composition comprising a pharmaceutically effective amount of one or more functional vasoactive intestinal peptide (VIP) fragments selected from the group consisting of VIP(4-16) (SEQ ID NO: 35), VIP(6-16) (SEQ ID NO: 72), VIP(6-10) (SEQ ID NO: 66), VIP(6-12) (SEQ ID NO: 68), VIP(10-28) (SEQ ID NO: 68), VIP(16-28), (SEQ ID NO: 88) VIP(6-20) (SEQ ID NO: 76) and VIP(6-24) (SEQ ID NO: 80), or conservative substitutions thereof.

Accordingly, in a fourth aspect the invention provides a composition for prophylactic or therapeutic treatment of myocardial fibrosis or an associated condition, the composition comprising a pharmaceutically effective amount of one or more functional vasoactive intestinal peptide (VIP) fragments selected from the group listed in Table 1, or conservative substitutions thereof.

The compositions of the invention may be administered in conjunction with a pharmaceutically acceptable carrier, which may be any of those known in the art or devised hereafter and suitable for the intended use. As well as carriers, the pharmaceutical composition of the invention may include other ingredients, including dyes, preservatives, buffers and anti-oxidants, for example. The compositions of the present invention may also include other active agents useful in the treatment of cardiovascular conditions.

The pharmaceutical composition of the invention may take any suitable form, but is preferably suitable for administration by oral, intravenous, intramuscular or subcuticular routes. Other methods of administration such as patches, snuffs, nasal sprays and the like will be clear to those skilled in the art.

According to a fifth aspect the invention provides a method of therapeutic treatment of myocardial fibrosis or an associated condition in a subject, the method including administering to the subject with myocardial fibrosis or an associated to condition, a composition according to the invention.

The compositions of the invention may be used to prevent or slow down progression of established myocardial fibrosis, as well as to reduce the degree of established fibrosis.

According to a sixth aspect the invention provides a method of prophylactic treatment of myocardial fibrosis or an associated condition in a subject, the method including administering to the subject at risk of developing myocardial fibrosis or an associated condition, a composition according to the invention.

With respect to prophylactic treatment it will be understood that such a treatment would benefit particularly subjects who are at risk of developing myocardial fibrosis or an associated condition. As an example of subjects in the risk category are those having hypertension, diabetes, myocarditis, ischaemic heart disease, drugs such as daunorubicin and others which are used in cancer chemotherapy, genetic predisposition, other conditions such as Conn's Syndrome and Phaeochromocytoma, high salt diet and the like. The prophylactic treatment may be used to prevent or slow down the development of fibrosis in the at risk group. High proportion of subjects may already have signs of early heart failure on echocardiography. For example such signs are present in nearly 80% of patients with hypertension. The incidence in diabetics is even higher.

According to a seventh aspect the invention provides a method of prophylactic or therapeutic treatment of congestive cardiac failure in a subject, the method including administering to the subject at risk of developing congestive cardiac failure, a pharmaceutical composition according to the invention.

According to a eighth aspect the invention provides a method of reducing the levels, inhibiting or reducing the production, of pro-fibrotic mediators in a subject, the method including administering to the subject a composition according to the invention.

According to an ninth aspect the invention provides a method of reducing collagen formation or enhancing collagen degradation in the cardiac muscle of a subject, the method including administering to the subject a composition according to the invention.

According to a tenth aspect the invention provides a method of therapeutic or prophylactic treatment of hypertension, the method including administering to the subject a composition according to the invention.

According to a eleventh aspect the invention provides a method of lowering blood pressure in a subject, the method including administering to a subject a a composition according to the invention.

It will be apparent to one skilled in the art that the pattern of use of the compositions of the invention may need to be altered for optimum effect. It may be necessary to take into account the nature of the disease or condition as well as its severity.

The associated conditions, which may be subject to prevention or treatment by the compositions of the invention, may include left ventricular hypertrophy, diastolic dysfunction, myocarditis, cardiomyopathy, left ventricular dysfunction and congestive cardiac failure (for which myocardial fibrosis may be an underlying pathology). The associated condition may also include conditions which give rise to generation of profibrotic mediators or conditions which predispose a subject to myocardial fibrosis, such as for example hypertension and/or high salt intake, diseases such as diabetes and the like.

Further aspect of the invention includes the use of a composition of the invention in the manufacture of a medicament for the prophylactic or therapeutic treatment of myocardial fibrosis, or an associated condition.

Yet another aspect of the invention provides the use of a composition of the invention in the manufacture of a medicament for the prophylactic or therapeutic treatment of congestive cardiac failure.

In another aspect, the invention relates to a composition comprising a pharmaceutically effective amount of one or more functional vasoactive intestinal peptide (VIP) fragments with the proviso that fragments VIP (1-12) (SEQ ID NO: 91) and VIP (6-28) (SEQ ID NO: 84) are not included.

In another aspect, the invention relates to a composition comprising a pharmaceutically effective amount of one or more functional vasoactive intestinal peptide (VIP) fragments having as a core sequence amino acid residues 6-10 or 16-25 of native VIP (SEQ ID NO: 1), or conservative substitutions thereof. Preferably, fragments VIP (1-12) (SEQ ID NO: 91) and VIP (6-28) (SEQ ID NO: 84) are not included.

Preferably, the VIP fragment is one or more fragments selected from the group consisting of: VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25) (SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88) or conservative substitutions thereof.

In another aspect, the invention relates to a composition for prophylactic or therapeutic treatment of myocardial fibrosis or an associated condition, the composition comprising a pharmaceutically effective amount of one or more functional vasoactive intestinal peptide (VIP) fragments wherein the VIP fragment is one or more fragments selected from the group consisting of: VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25)

(SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88) or conservative substitutions thereof.

In another aspect, the invention relates to a composition for prophylactic or therapeutic treatment of hypertension, the composition comprising a pharmaceutically effective amount of one or more functional vasoactive intestinal peptide (VIP) fragments wherein the VIP fragment is one or more fragments selected from the group consisting of: VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25) (SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88) or conservative substitutions thereof.

Preferably, compositions according to the present invention are administered in conjunction with a pharmaceutically acceptable carrier. They may preferably be administered in conjunction with one or more other active agents useful in the treatment of cardiovascular conditions. They may, for preference, be formulated for administration by oral, intravenous, intramuscular or subcuticular routes.

In another aspect, the invention relates to method of therapeutic or prophylactic treatment of myocardial fibrosis or an associated condition in a subject, the method including administering to a subject a composition including a pharmaceutically effective amount of one or more functional vasoactive intestinal peptide (VIP) fragments having as a core sequence amino acid residues 6-10 or 16-25 of native VIP (SEQ ID NO: 1), or conservative substitutions thereof.

In another aspect, the invention relates to a method of therapeutic or prophylactic treatment of myocardial fibrosis or an associated condition in a subject, the method including administering to a subject a composition according to the present invention.

In another aspect, the invention relates to a method of therapeutic or prophylactic treatment of myocardial fibrosis or an associated condition in a subject, the method including administering to a subject a composition including one or more VIP fragments selected from the group consisting of VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25) (SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88) or conservative substitutions thereof.

Preferably, the method is used to prevent or slow down progression of established myocardial fibrosis, or alternatively, to reduce the degree of established fibrosis.

Preferably the associated condition is hypertension, diabetes, myocarditis, ischaemic heart disease, left ventricular hypertrophy, diastolic dysfunction, myocarditis, cardiomyopathy, left ventricular dysfunction, congestive cardiac failure (for which myocardial fibrosis may be an underlying pathology), treatment with drugs such as daunorubicin and others which are used in cancer chemotherapy, genetic predisposition, other conditions such as Conn's Syndrome and Phaeochromocytoma, high salt diet and the like.

Preferably the associated condition includes conditions which give rise to generation of profibrotic mediators or conditions which predispose a subject to myocardial fibrosis.

Preferably the prophylactic treatment is used to prevent or slow down the development of fibrosis in the at risk group.

Preferably the condition is hypertension and/or high salt intake, diseases such as diabetes and the like. Most preferably, the condition is hypertension.

In another aspect, the invention relates to method of therapeutic or prophylactic treatment of myocardial fibrosis by reducing hypertension, the method including administering to a subject in need or at risk a composition including a VIP fragment.

In another aspect, the invention relates to a method of therapeutic or prophylactic treatment of myocardial fibrosis by reducing hypertension, the method including administering an associated condition a composition including one or more VIP fragments selected from the group consisting of VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25) (SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88) or conservative substitutions thereof.

Preferably, the method is used to prevent or slow down progression of established myocardial fibrosis.

Preferably the method is used to reduce the degree of established fibrosis.

In another aspect, the invention relates to method of lowering blood pressure comprising administering to a subject in need thereof a composition including a pharmaceutically effective amount of one or more of vasoactive intestinal peptide (VIP) and/or active fragment thereof with a pharmaceutically acceptable carrier.

In another aspect, the invention relates to a method of lowering blood pressure comprising administering to a subject in need thereof a composition including a pharmaceutically effective amount of one or more functional vasoactive intestinal peptide (VIP) fragments having as a core sequence amino acid residues 6-10 or 16-25 of native VIP (SEQ ID NO: 1), or conservative substitutions thereof.

In another aspect, the invention relates to a method of lowering blood pressure, the method including administering to a subject a composition including one or more VIP fragments selected from the group consisting of VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25) (SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88) or conservative substitutions thereof.

In another aspect, the invention relates to a method of treating hypertension comprising administering to a subject in need thereof a composition including a pharmaceutically effective amount of one or more functional vasoactive intestinal peptide (VIP) fragments having as a core sequence amino acid residues 6-10 or 16-25 of native VIP (SEQ ID NO: 1), or conservative substitutions thereof.

In another aspect, the invention relates to a method of treating hypertension comprising administering to a subject in need thereof a composition including a pharmaceutically effective amount of one or more functional vasoactive intestinal peptide (VIP) fragments having as a core sequence amino acid residues 6-10 or 16-25 of native VIP (SEQ ID NO: 1), or conservative substitutions thereof.

In another aspect, the invention relates to a method of therapeutic or prophylactic treatment of hypertension, the method including administering to a subject a composition including one or more VIP fragments selected from the group consisting of VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25) (SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88) or conservative substitutions thereof.

Preferably, the subject has myocardial fibrosis or an associated condition.

In another aspect, the invention relates to a method of reducing the levels, inhibiting or reducing the production of pro-fibrotic mediators in a subject, the method including administering to the subject a composition according to the present invention.

In another aspect, the invention relates to a method of reducing collagen formation or enhancing collagen degradation in the cardiac muscle of a subject, the method including administering to the subject a composition according to the invention In another aspect, the invention relates to the use of a composition according to the invention for the manufacture of a medicament for the treatment or prophylaxis of myocardial fibrosis or an associated condition Preferably, the use is to prevent or slow down progression of established myocardial fibrosis. Alternatively, the use is to prevent or slow down the development of fibrosis in an at risk group. Also preferably, the use is to reduce the degree of established fibrosis.

Preferably, the associated condition is hypertension, diabetes, myocarditis, ischaemic heart disease, left ventricular hypertrophy, diastolic dysfunction, myocarditis, cardiomyopathy, left ventricular dysfunction, congestive cardiac failure (for which myocardial fibrosis may be an underlying pathology), treatment with drugs such as daunorubicin and others which are used in cancer chemotherapy, genetic predisposition, other conditions such as Conn's Syndrome and Phaeochromocytoma, high salt diet and the like.

Preferably, the associated condition includes conditions which give rise to generation of profibrotic mediators or conditions which predispose a subject to myocardial fibrosis. Preferably, the condition is hypertension and/or high salt intake, diseases such as diabetes and the like.

In another aspect, the invention relates to the use of a composition including one or more VIP fragments selected from the group consisting of VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25) (SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88) or conservative substitutions thereof in the manufacture of a medicament for the therapeutic or prophylactic treatment of myocardial fibrosis or an associated condition.

In another aspect, the invention relates to the use of a composition including one or more VIP fragments selected from the group consisting of VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25) (SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88) or conservative substitutions thereof in the manufacture of a medicament for the therapeutic or prophylactic treatment of myocardial fibrosis by reducing hypertension.

In another aspect, the invention relates to the use of VIP or a fragment thereof in the manufacture of a medicament for lowering blood pressure in a subject. Preferably, the VIP fragment is one or more VIP fragments selected from the group consisting of VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25)

(SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88).

In another aspect, the invention relates to the use of a VIP in the manufacture of a medicament for the therapeutic or prophylactic treatment of hypertension. Preferably the VIP fragment is one or more VIP fragments selected from the group consisting of VIP(4-10) (SEQ ID NO: 29), VIP(4-11) (SEQ ID NO: 30), VIP(4-12) (SEQ ID NO: 31), VIP(4-13) (SEQ ID NO: 32), VIP(4-14) (SEQ ID NO: 33), VIP(4-15) (SEQ ID NO: 34), VIP(4-16) (SEQ ID NO: 35), VIP(4-17) (SEQ ID NO: 36), VIP(4-18) (SEQ ID NO: 37), VIP(4-19) (SEQ ID NO: 38), VIP(4-20) (SEQ ID NO: 39), VIP(4-21) (SEQ ID NO: 40), VIP(4-22) (SEQ ID NO: 41), VIP(4-23) (SEQ ID NO: 42), VIP(4-24) (SEQ ID NO: 43), VIP(4-25) (SEQ ID NO: 44), VIP(4-26) (SEQ ID NO: 45), VIP(4-27) (SEQ ID NO: 46), VIP(4-28) (SEQ ID NO: 90), VIP(5-10) (SEQ ID NO: 47), VIP(5-11) (SEQ ID NO: 48), VIP(5-12) (SEQ ID NO: 49), VIP(5-13) (SEQ ID NO: 50), VIP(5-14) (SEQ ID NO: 51), VIP(5-15) (SEQ ID NO: 52), VIP(5-16) (SEQ ID NO: 53), VIP(5-17) (SEQ ID NO: 54), VIP(5-18) (SEQ ID NO: 55), VIP(5-19) (SEQ ID NO: 56), VIP(5-20) (SEQ ID NO: 57), VIP(5-21) (SEQ ID NO: 58), VIP(5-22) (SEQ ID NO: 59), VIP(5-23) (SEQ ID NO: 60), VIP(5-24) (SEQ ID NO: 61), VIP(5-25) (SEQ ID NO: 62), VIP(5-26) (SEQ ID NO: 63), VIP(5-27) (SEQ ID NO: 64), VIP(5-28) (SEQ ID NO: 65), VIP(6-10) (SEQ ID NO: 66), VIP(6-11) (SEQ ID NO: 67), VIP(6-12) (SEQ ID NO: 68), VIP(6-13) (SEQ ID NO: 69), VIP(6-14) (SEQ ID NO: 70), VIP(6-15) (SEQ ID NO: 71), VIP(6-16) (SEQ ID NO: 72), VIP(6-17) (SEQ ID NO: 73), VIP(6-18) (SEQ ID NO: 74), VIP(6-19) (SEQ ID NO: 75), VIP(6-20) (SEQ ID NO: 76), VIP(6-21) (SEQ ID NO: 77), VIP(6-22) (SEQ ID NO: 78), VIP(6-23) (SEQ ID NO: 79), VIP(6-24) (SEQ ID NO: 80), VIP(6-25) (SEQ ID NO: 81), VIP(6-26) (SEQ ID NO: 82), VIP(6-27) (SEQ ID NO: 83), VIP(10-28) (SEQ ID NO: 92), VIP(16-25) (SEQ ID NO: 85), VIP(16-26) (SEQ ID NO: 86), VIP(16-27) (SEQ ID NO: 87), VIP(16-28) (SEQ ID NO: 88).

DESCRIPTION OF THE PREFERRED EMBODIMENT

Figure 1:
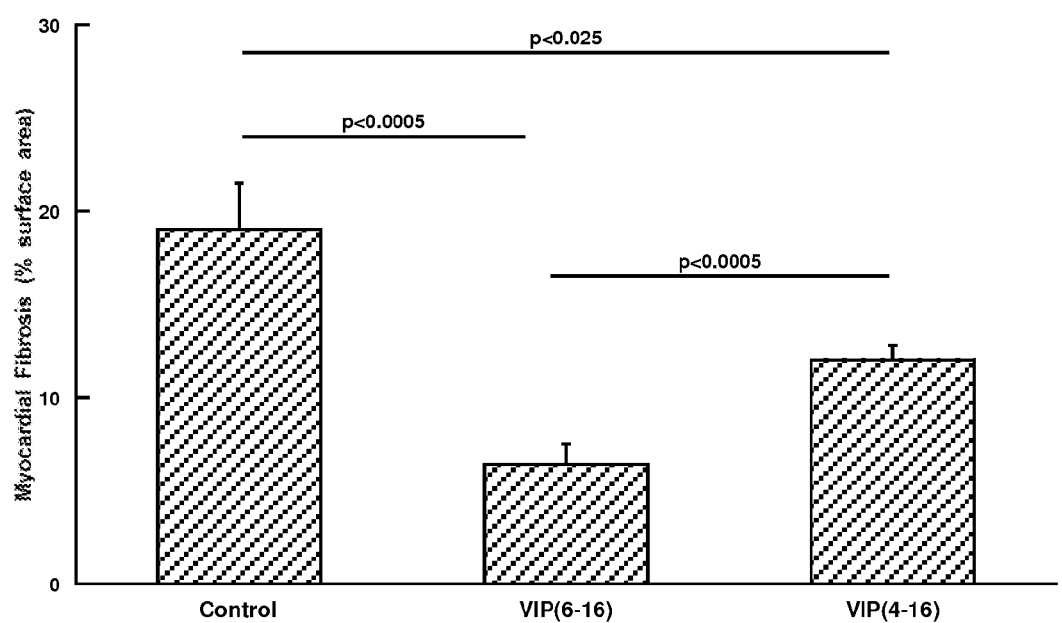
FIG. 1: Comparison of the degree of myocardial fibrosis in WKY rats on a high salt diet after 4 week infusion of vehicle, VIP(6-16) (SEQ ID NO: 72) or VIP(4-16) (SEQ ID NO: 35).

It has now been found, quite surprisingly in view of the well accepted views held in this field, that VIP fragments lacking amino acids and motifs thought to be important for their function are nevertheless useful therapeutic agents to reverse or delay onset of myocardial fibrosis, or prevent onset of fibrosis in subjects at risk of developing myocardial fibrosis. Thus, VIP fragments are also useful in the treatment of congestive cardiac failure.

The use of the pharmaceutical compositions of the invention in the treatment of myocardial fibrosis or associated conditions represents a new class of therapeutic agents for these conditions. Existing treatments for myocardial fibrosis or associated conditions usually target one, or at the most two, of the known causative mechanisms in myocardial fibrosis. Without wishing to be bound by any particular mechanism of action, it is believed that the pharmaceutical preparations of the invention may target virtually all the currently known promoters of myocardial fibrosis.

On the basis of the present studies, and not wishing to be bound by theory, it is postulated that VIP fragments act as a major regulator to prevent the development of fibrosis and that the depletion of VIP may unleash the synthesis of a number of profibrotic mediators, thereby causing myocardial injury. The VIP fragments of the present invention seem to be able to act in much the same way as the native VIP but are more suited for therapeutic applications due to smaller size and hence increased stability and ease of manufacture.

Further, and unexpectedly, a number of fragments lacking certain amino acid residues and domains commonly thought to be important for its function have been shown to be active in the present studies. Particularly useful fragments are VIP (6-16) (SEQ ID NO: 72), VIP(16-28) (SEQ ID NO: 88), VIP(10-28) (SEQ ID NO: 92), VIP(6-12) (SEQ ID NO: 68), VIP(6-10) (SEQ ID NO: 66), VIP(6-20) (SEQ ID NO: 76), VIP(6-24) (SEQ ID NO: 80) and VIP(4-16) (SEQ ID NO: 35). Further, fragments listed in Table 1 are also expected to be useful in the methods of the present invention. Fragments VIP(1-12) (SEQ ID NO: 91) and VIP(6-28) (SEQ ID NO: 84) have been described earlier and are not included in the present invention. It will be understood that the present invention also encompasses within its scope certain analogues of the VIP fragments which are based on conservative substitution of one or more amino acids of the VIP fragments with amino acids which do not alter the biological activities of the VIP fragments. Such substitutions would be well known to those skilled in the art and would not require more than simple trial-and-error using well established techniques. Hence, the term "VIP fragment" as used in the context of the present invention is intended to encompass such analogues.

Other useful VIP fragments are listed in Table 1. All the sequences relate to VIP and fragments of human origin but due to the very high level of amino acid conservation, VIP and fragments thereof derived from other mammalian species are also contemplated and encompassed by the present invention.

The present invention also contemplates pharmaceutical compositions which include active VIP fragments. Such compositions may include any type of dosage form such as tablets, capsules, powders, liquid formulations, delayed or sustained release, patches, snuffs, nasal sprays and the like. The formulations may additionally include other ingredients such as dyes, preservatives, buffers and anti-oxidants, for example. The physical form and content of the pharmaceutical formulations contemplated are conventional preparations that can be formulated by those skilled in the pharmaceutical formulation field and are based on well established principles and compositions described in, for example, Remington: The Science and Practice of Pharmacy, 19$^{th}$ Edition, 1995; British Pharmacopoeia 2000 and similar formulation texts and manuals. The compositions of the present invention may also include other active agents useful in the treatment of cardiovascular conditions.

The route and frequency of administration of the compositions of the present invention will depend on the treatment requirements and the nature of the molecule to be administered. Thus the formulations may be suitably prepared for administration by intravenous, intramuscular or subcuticular injection. VIP fragments may also be suitable for mucosal administration such as oral, sublingual, nasal and the like. These parameters are easily established by those skilled in the art.

The pharmaceutical compositions of the invention have been shown to be effective in preventing or slowing down progression of established myocardial fibrosis, as well as in reducing the degree (reversal) of established fibrosis and thus important in therapeutic applications. The compositions of the present invention are also useful for prophylactic or therapeutic treatment of congestive cardiac failure. These are important findings with respect to the range and severity of conditions which can be treated with the compositions of the present invention.

Further, the compositions of the present invention may be used prophylactically in subjects at risk of developing myocardial fibrosis or an associated condition. As an example of subjects in the risk category are those having hypertension, diabetes, myocarditis, ischaemic heart disease, drugs such as daunorubicin and others which are used in cancer chemotherapy, genetic predisposition, other conditions such as Conn's Syndrome and Phaeochromocytoma, high salt diet and the like. The term "prophylactic" as used in the context of the present invention is intended inter alia to encompass treatments used to prevent or slow down the development of fibrosis in the at risk group. High proportion of subjects which may be given prophylactic treatment may already have signs of early heart failure on echocardiography.

The term "associated condition" as used in the context of the present invention and in reference to myocardial fibrosis is intended to encompass, without limitation, left ventricular hypertrophy, diastolic dysfunction, myocarditis, cardiomyopathy, left ventricular dysfunction and congestive cardiac failure (for which myocardial fibrosis may be an underlying pathology). The associated condition may also include conditions which give rise to generation of profibrotic mediators or conditions which predispose a subject to myocardial fibrosis, such as for example hypertension and/or high salt intake, diseases such as diabetes and the like.

By conserving the VIP content of the cardiac muscle in a subject with, or at risk of developing, myocardial fibrosis or associated condition, through the use of the compositions of the present invention significant therapeutic benefits can be achieved including reduction of fibrosis, reduction in the level, production or activity of pro-fibrotic mediators, reduction in progression of fibrosis, reduction in collagen formation or enhancing collagen degradation in the cardiac muscle.

The invention will now be described more particularly with reference to non-limiting examples.

EXPERIMENTAL

All general methodology and techniques have been described in detail in PCT/AU2005/000835, incorporated in its entirety herein by reference.

Example 1

Effect of VIP Fragment Infusion on Fibrosis in Animal Models of Fibrosis

Four animal models of myocardial fibrosis were used (animals obtained from Australian Animal Resources, Perth, Western Australia, Australia)
i) WKY rat fed a high salt diet
ii) WKY rat fed a high salt diet and given L-NAME (co-monomethyl-nitro-L-arginine, Sigma Chemical Co.) 10 mg/kg/day in the drinking water
iii) WKY rats with diabetes induced by streptozotocin injection 60 mg/kg
iv) SHR rat fed a 2.2% salt diet for 4 weeks In each model the rats were randomised to VIP(4-16) (Ala-Val-Phe-Thr-Asp-Asn-Tyr-Thr-Arg-Leu-Arg-Lys-Gln) (SEQ ID NO: 35), VIP(6-16) (Phe-Thr-Asp-Asn-Tyr-Thr-Arg-Leu-Arg-Lys-Gln) (SEQ ID NO: 72), VIP(4-20) (Ala-Val-Phe-Thr-Asp-Asn-Tyr-Thr-Arg-Leu-Arg-Lys-Gln-Met- Ala-Val-Lys-) (SEQ ID NO: 39), or VIP(4-24) (Ala-Val-Phe-Thr-Asp-Asn-Tyr-Thr-Arg-Leu-Arg-Lys-Gln-Met-Ala-Val-Lys-Lys-Tyr-Leu-Asn) (SEQ ID NO: 43), VIP(16-28) (Gln-Met-Ala-Val-Lys-Tyr-Leu-Asn-Ser-Ile-Leu-Asn) (SEQ ID NO: 88), VIP(10-28) (Tyr-Thr-Arg-Leu-Arg-Lys-Gln-Met-Ala-Val-Lys-Lys-Tyr-Leu-Asn-Ser-Ile-Leu-Asn) (SEQ ID NO: 92), VIP(6-12) (Phe-Thr-Asp-Asn-Tyr-Thr-Arg) (SEQ ID NO: 68), VIP(6-10) (Phe-Thr-Asp-Asn-Tyr) (SEQ ID NO: 66), VIP(6-20) (Phe-Thr-Asp-Asn-Tyr-Thr-Arg-Leu-Arg-Lys-Gln-Met-Ala-Val-Lys-) (SEQ ID NO: 76), or VIP(6-24) (Phe-Thr-Asp-Asn-Tyr-Thr-Arg-Leu-Arg-Lys-Gln-Met-Ala-Val-Lys-Lys-Tyr-Leu-Asn) (SEQ ID NO: 80) (All obtained from or synthesised by Auspep, Australia) or vehicle control (Hartman's Solution, Baxter) infusion for 4 weeks via Alzet minipump (n=6-8 each experimental group). The dose of each peptide was 5 pmol/kg/min.

In models i) and ii) 14 week old WKY rats were commenced on high salt diet or high salt diet plus L-NAME. They underwent operative insertion of an Alzet minipump for infusion of VIP or vehicle. After 4 weeks the rats were anaesthetised and the hearts harvested. Myocardial fibrosis levels were quantitated.

In model iii) rats are injected with streptozotocin 60 mg/kg at 14 weeks of age. After 8 weeks the diabetic rats are randomised to peptide infusion (5 pmol/kg/min) or no treatment. The peptides are administered as above. After a further 4 weeks the rats are anaesthetised and the hearts harvested as above.

In model iv) 14 week old SHR rats are commenced on a 2.2% salt diet. They undergo operative insertion of an Alzet minipump for peptide or vehicle infusion. After 4 weeks the rats are anaesthetised and the hearts harvested. Myocardial fibrosis levels are quantitated as above.

The degree of myocardial fibrosis is quantitated by two methods in known manner (refer Ye V Z C, Hodge G, Yong J L C & Duggan K A (2002) Early myocardial fibrosis is associated with depletion of vasoactive intestinal peptide in the heart Exp. Physiol 87:539-546 Ye V Z C, Hodge G, Yong J L C & Duggan K A (2003) Myocardial VIP and myocardial fibrosis induced by nitric oxide synthase inhibition in the rat Acta Physiol. Scand. 179:353-360. Ye V Z C, Hodge G, Yong J L C & Duggan K A (2004) Vasopeptidase inhibition reverses myocardial VIP depletion and decreases myocardial fibrosis in salt sensitive hypertension Europ. J. Pharmacol. 485:235-242).

A significant improvement was found in the hearts of the treated rats in that the myocardial fibrosis index was significantly lower in the treated rats compared to the control groups (FIG. 1).

Example 2

Effect of VIP Fragment Treatment on Regression of Fibrosis in Animal Models of Fibrosis To determine whether VIP (6-16) (SEQ ID NO: 72), VIP (6-20) (SEQ ID NO: 76) and VIP(6-24) (SEQ ID NO: 80) infusion caused regression of existing fibrosis as well as prevented progression of fibrosis two groups of studies were performed. The degree of myocardial fibrosis in untreated 14 week old WKY rats was compared with the degree of fibrosis in 18 week old WKY rats after 4 weeks treatment with a high salt diet or a high salt diet plus L-NAME (10 mg/kg/day) and either VIP (6-16) (SEQ ID NO: 72), VIP(6-20) (SEQ ID NO: 76) and VIP(6-24) (SEQ ID NO: 80) (5 pmol/kg/min) or vehicle control infusion (see FIG. 2)

Figure 2:
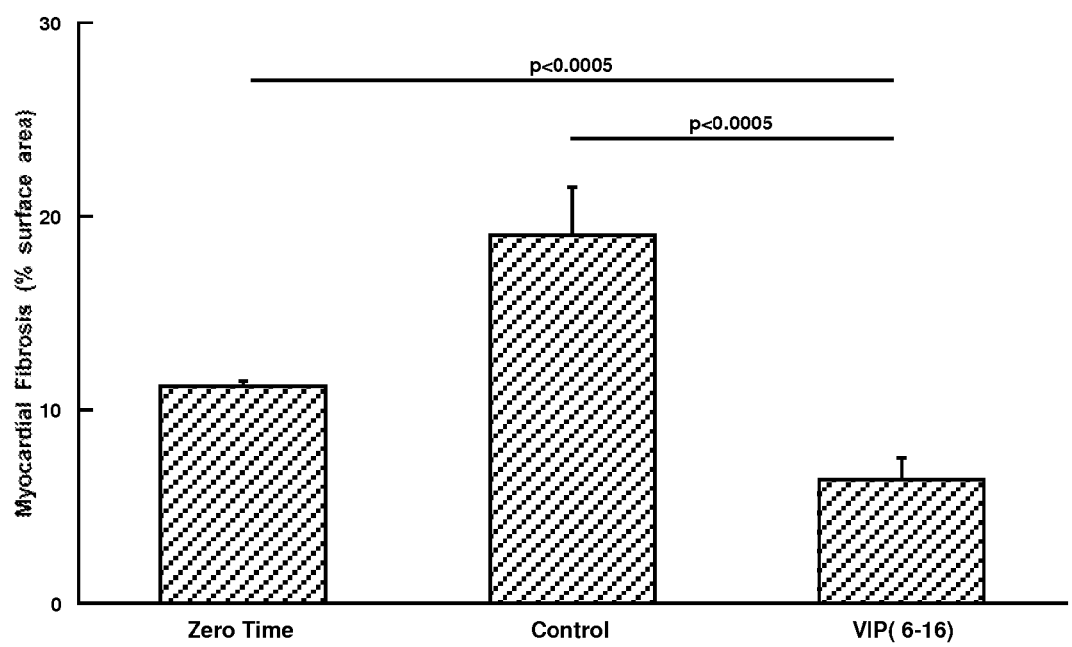
FIG. 2: Comparison of myocardial fibrosis in rats aged 14 weeks (zero time) then on a high salt diet for 4 weeks and receiving either vehicle infusion or VIP(6-16) (SEQ ID NO: 72) infusion (5 pmol/kg/min) for 4 weeks).
Figure 3:
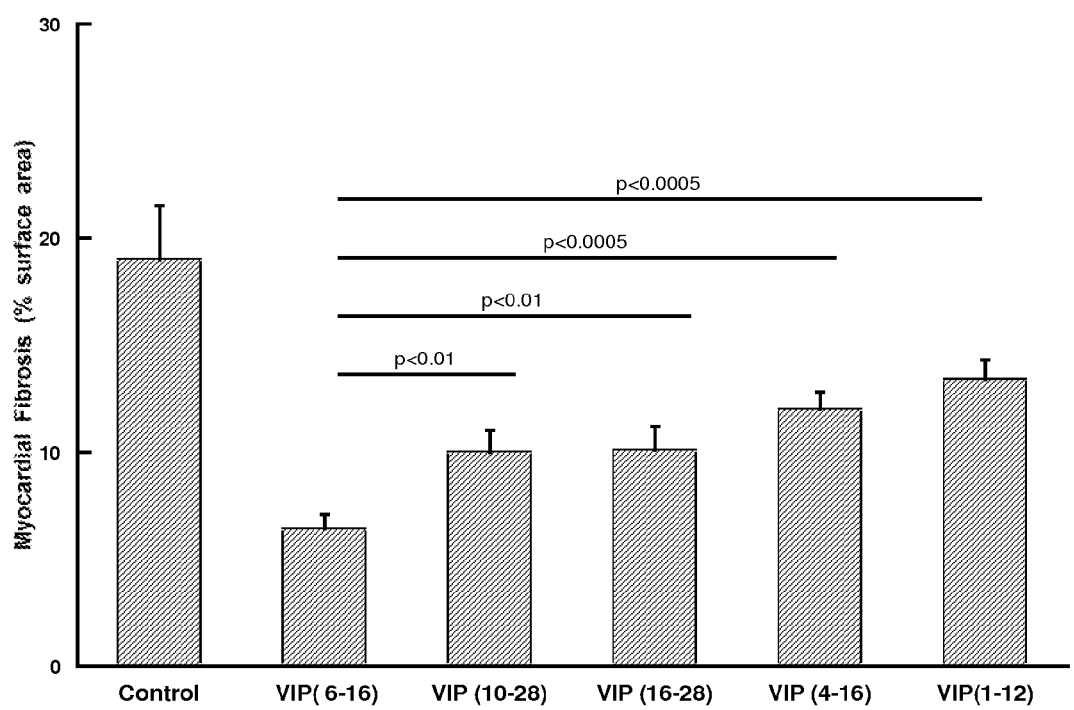
FIG. 3: Myocardial fibrosis in 18 week old WKY rats after 4 weeks on a high salt diet and treated with VIP(6-16) (SEQ ID NO: 72), VIP(10-28) (SEQ ID NO: 92), VIP(16-28) (SEQ ID NO: 88), VIP(4-16) (SEQ ID NO: 35) and VIP(1-12) (SEQ ID NO: 91) or vehicle Control. All peptides were infused at a dose of 5 pmol/kg/min for 4 weeks.
Figure 4:
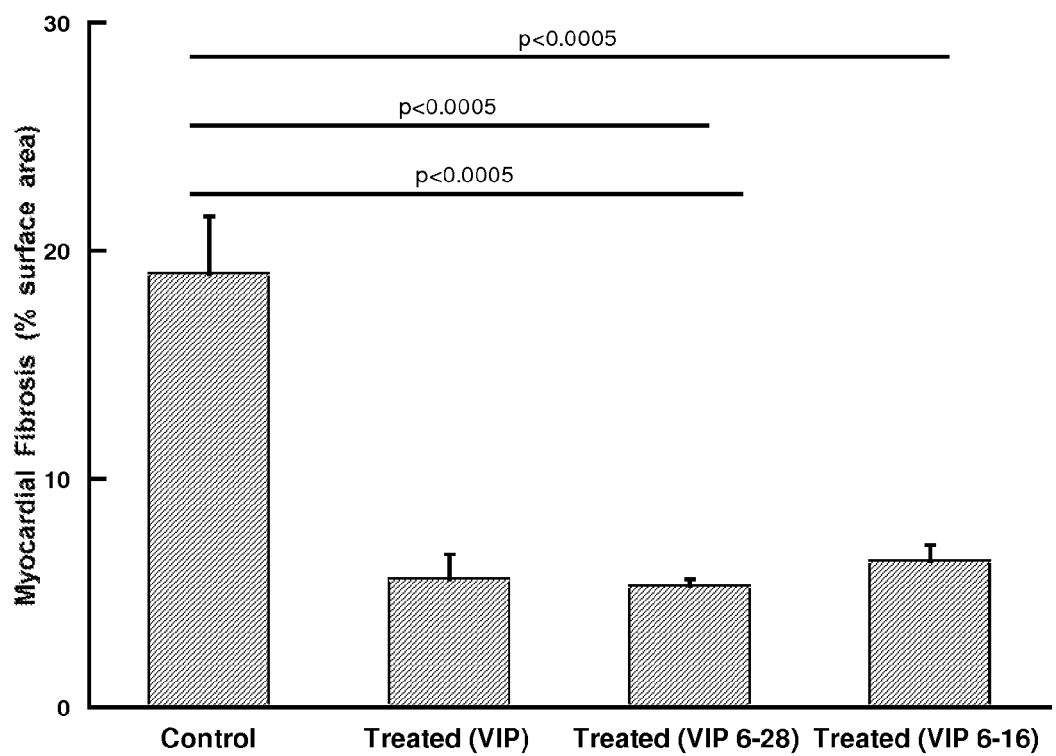
FIG. 4: Myocardial fibrosis in 18 week old WKY rats after 4 weeks on a high salt diet and treated with native VIP(SEQ ID NO: 1), VIP(6-28) (SEQ ID NO: 84), VIP(6-16) (SEQ ID NO: 72), or vehicle Control. All peptides were infused at a dose of 5 pmol/kg/min for 4 weeks.
Figure 5:
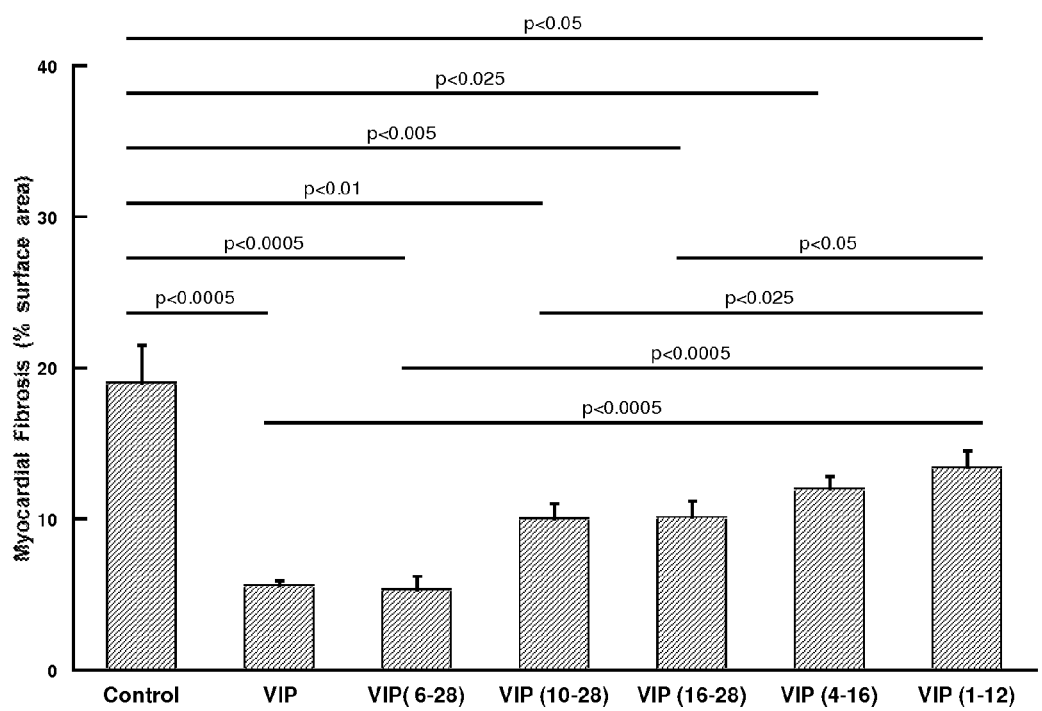
FIG. 5: Myocardial fibrosis in 18 week old WKY rats after 4 weeks on a high salt diet and treated with native VIP(SEQ ID NO: 1), VIP(6-28) (SEQ ID NO: 84), VIP(10-28) (SEQ ID NO: 92), VIP(16-28) (SEQ ID NO: 88), VIP(4-16) (SEQ ID NO: 35) and VIP(1-12) (SEQ ID NO: 92) or vehicle Control. All peptides were infused at a dose of 5 pmol/kg/min for 4 weeks.

Preliminary results are shown in FIG. 2. The data clearly show regression of myocardial fibrosis following VIP(6-16) (SEQ ID NO: 72) infusion. The regression of fibrosis may be due to either reduction in collagen formation or enhancement of its degradation. Although not wishing to be bound by any particular mechanism of action, the regression of myocardial fibrosis is likely to be due to the action of collagenases, which play a part in collagen resorption.

The importance of the present invention to health care will be immediately apparent to one skilled in the art upon reading this disclosure. Although the capacity to treat cardiac failure has improved significantly with the advent of angiotensin converting enzyme (ACE) inhibitors and angiotensin receptor blockers, as well as the realisation that aldosterone antagonists and beta blockers improve outcome in later stage disease, the addition of the pharmaceutical preparations of the invention, which act to prevent the progression of the underlying lesion (fibrosis), or even reverse fibrosis, has the capacity to prevent the escalation of mild to severe disease and hence to substantially reduce the health care burden. The overall size of certain VIP fragments and their activity makes them ideally suitable as targets for drug development.

Example 3

Effect of VIP Fragment Treatment on Blood Pressure in Animal Models of Hypertension To determine whether VIP and fragments were effective in controlling blood pressure, Spontaneous Hypertensive Rats (SHR) were acclimated to blood pressure measurement by tail cuff plethysmography and then they were placed on a 2.2% salt diet for 4 weeks.

The rats were randomized to Control (Hartman's Solution) vehicle infusion, VIP(1-28) (His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn) (SEQ ID NO: 1), VIP(4-10) (Ala-Val-Phe-Thr-Asp-Asn-Tyr) (SEQ ID NO: 29), VIP (4-12) (Ala-Val-Phe-Thr-Asp-Asn-Tyr-Thr-Arg) (SEQ ID NO: 31), VIP(4-16) (Ala-Val-Phe-Thr-Asp-Asn-Tyr-Thr-Arg-Leu-Arg-Lys-Gln) (SEQ ID NO: 35), VIP(4-20) (Ala-Val-Phe-Thr-Asp-Asn-Tyr-Thr-Arg-Leu-Arg-Lys-Gln-Met-Ala-Val-Lys) (SEQ ID NO: 39), VIP(4-24) (Ala-Val-Phe-Thr-Asp-Asn-Tyr-Thr-Arg-Leu-Arg-Lys-Gln-Met-Ala-Val-Lys-Lys-Tyr-Leu-Asn) (SEQ ID NO: 43), VIP(4-28) (Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn) (SEQ ID NO: 90), VIP(6-10) (Phe-Thr-Asp-Asn-Tyr) (SEQ ID NO: 66), VIP(6-12) (Phe-Thr-Asp-Asn-Tyr-Thr-Arg) (SEQ ID NO: 68), VIP(6-16) (Phe-Thr-Asp-Asn-Tyr-Thr-Arg-Leu-Arg-Lys-Gln) (SEQ ID NO: 72), VIP(6-20) (Phe-Thr-Asp-Asn-Tyr-Thr-Arg-Leu-Arg-Lys-Gln-Met-Ala-Val-Lys) (SEQ ID NO: 76), VIP(6-24) (Phe-Thr-Asp-Asn-Tyr-Thr-Arg-Leu-Arg-Lys-Gln-Met-Ala-Val-Lys-Lys-Tyr-Leu-Asn) (SEQ ID NO: 80), VIP(6-28) (Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn) (SEQ ID NO: 84), VIP(16-20) (Gln-Met-Ala-Val-Lys) (SEQ ID NO: 20), VIP(16-24) (Gln-Met-Ala-Val-Lys-Lys-Tyr-Leu-Asn) (SEQ ID NO: 93), VIP(16-28) (Gln-Met-Ala-Val-Lys-Lys-Tyr-Leu-Asn-Ser-Ile-Leu-Asn) (SEQ ID NO: 88), VIP(1-12) (His-Ser-Asp-Ala-Val-Phe-Thr-Asp-Asn-Tyr-Thr-Arg) (SEQ ID NO: 91) and VIP(10-28) (Tyr-Thr-Arg-Leu-Arg-Lys-Gln-Met-Ala-Val-Lys-Lys-Tyr-Leu-Asn-Ser-Ile-Leu-Asn) (SEQ ID NO: 92), VIP(4-10) (Ala-Val-Phe-Thr-Asp-Asn-Tyr) (SEQ ID NO: 29).

Each peptide was infused at 5 pmol/kg/min

Blood pressure was measured by tail cuff plethysmography twice weekly for 4 weeks.

The resultant systolic blood pressure (SBP) measurements are shown in FIGS. 6-9. Several of the fragments showed a reduction in SPB relative to the control solution. VIP itself was not seen to have any significant effect in reducing SBP, but a number of fragments, notably VIP(6-28) (SEQ ID NO: 84), VIP(4-24) (SEQ ID NO: 43), VIP(4-28) (SEQ ID NO: 90), and more particularly VIP(4-16) (SEQ ID NO: 35), VIP (4-12) (SEQ ID NO: 31), VIP(4-20) (SEQ ID NO: 39), VIP (6-20) (SEQ ID NO: 76) and VIP(6-24) (SEQ ID NO: 80) achieved significant reductions in SBP.

Figure 6:
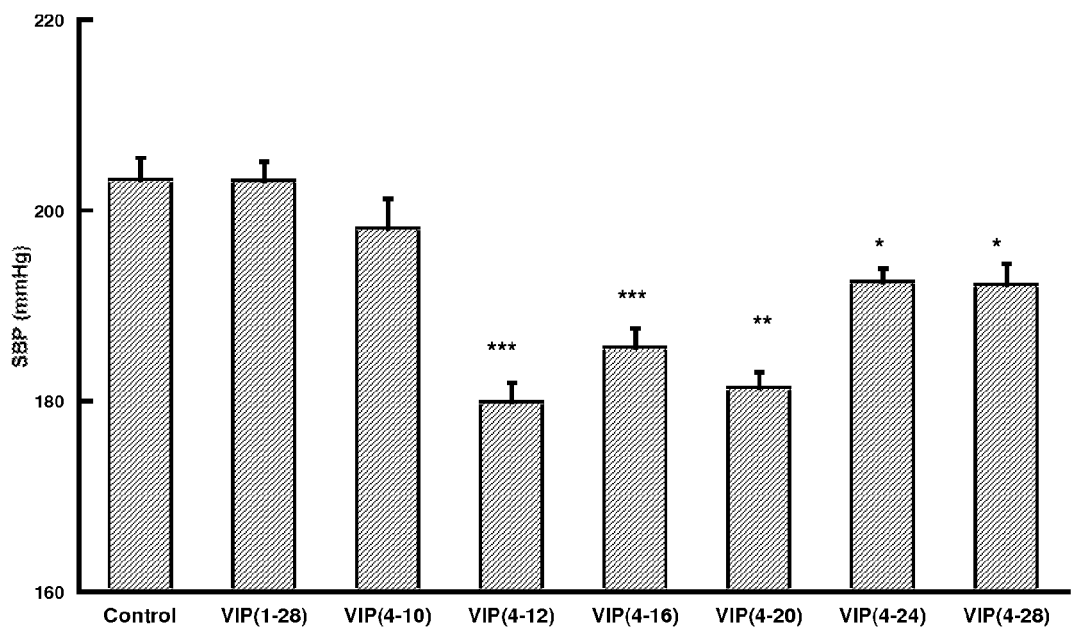
FIG. 6: Systolic blood pressure (SBP) in SHR after 4 weeks on a high salt diet and treated with VIP(1-28) (SEQ ID NO: 1), VIP(4-10) (SEQ ID NO: 29), VIP(4-12) (SEQ ID NO: 31), VIP(4-16) (SEQ ID NO: 35), VIP(4-20) (SEQ ID NO: 39), VIP(4-24) (SEQ ID NO: 43) and VIP(4-28) (SEQ ID NO: 90) or control. All peptides were infused at a dose of 5 pmol/kg/min for 4 weeks.
Figure 7:
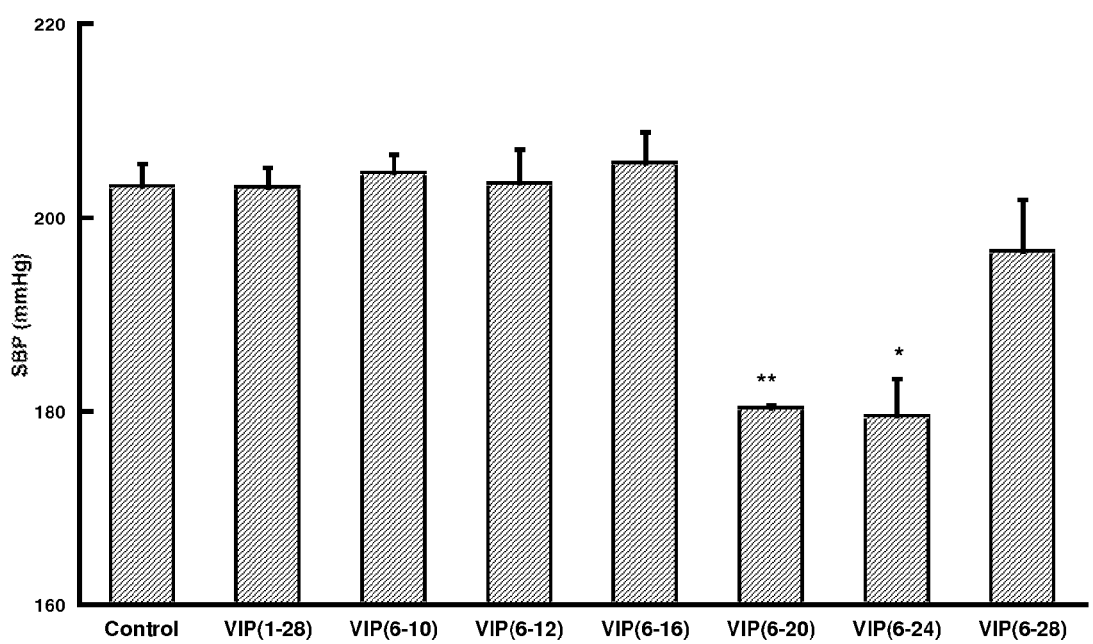
FIG. 7: Systolic blood pressure (SBP) in SHR after 4 weeks on a high salt diet and treated with VIP(1-28) (SEQ ID NO: 1), VIP(6-10) (SEQ ID NO: 66), VIP(6-12) (SEQ ID NO: 68), VIP(6-16) (SEQ ID NO: 72), VIP(6-20) (SEQ ID NO: 76), VIP(6-24) (SEQ ID NO: 80) and VIP(6-28) (SEQ ID NO: 84) or control. All peptides were infused at a dose of 5 pmol/kg/min for 4 weeks.
Figure 8:
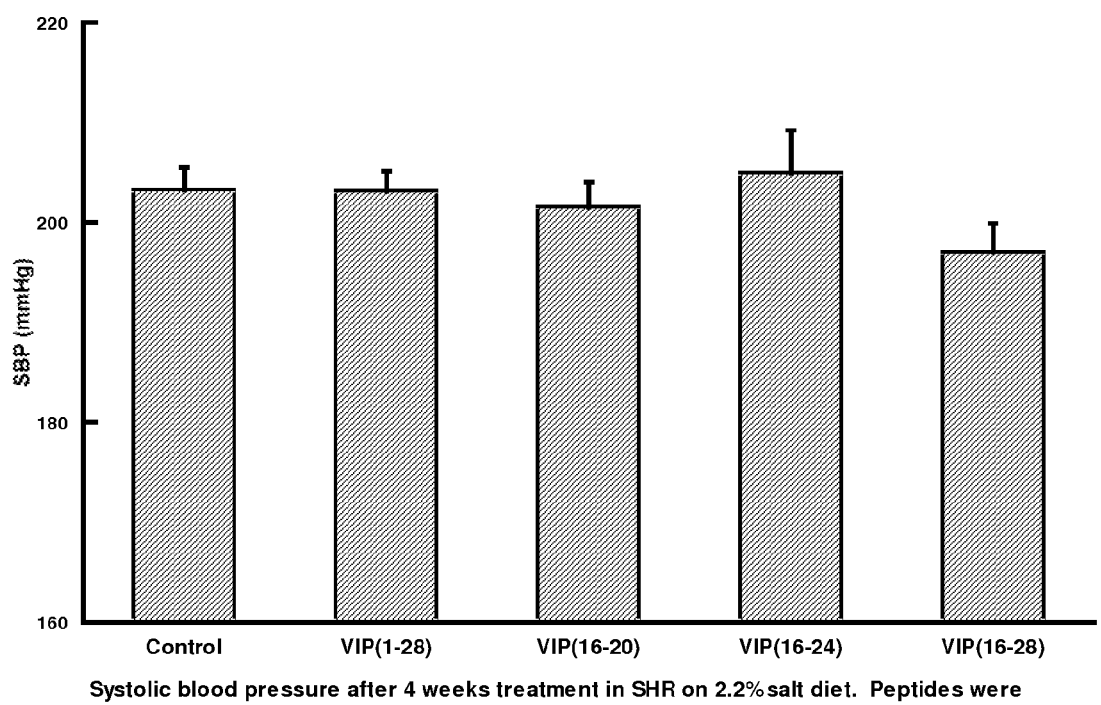
FIG. 8: Systolic blood pressure (SBP) in SHR after 4 weeks on a high salt diet and treated with VIP(1-28) (SEQ ID NO: 1), VIP(16-20) (SEQ ID NO: 20), VIP(16-24) (SEQ ID NO: 93) and VIP(16-28) (SEQ ID NO: 88) or control. All peptides were infused at a dose of 5 pmol/kg/min for 4 weeks.
Figure 9:
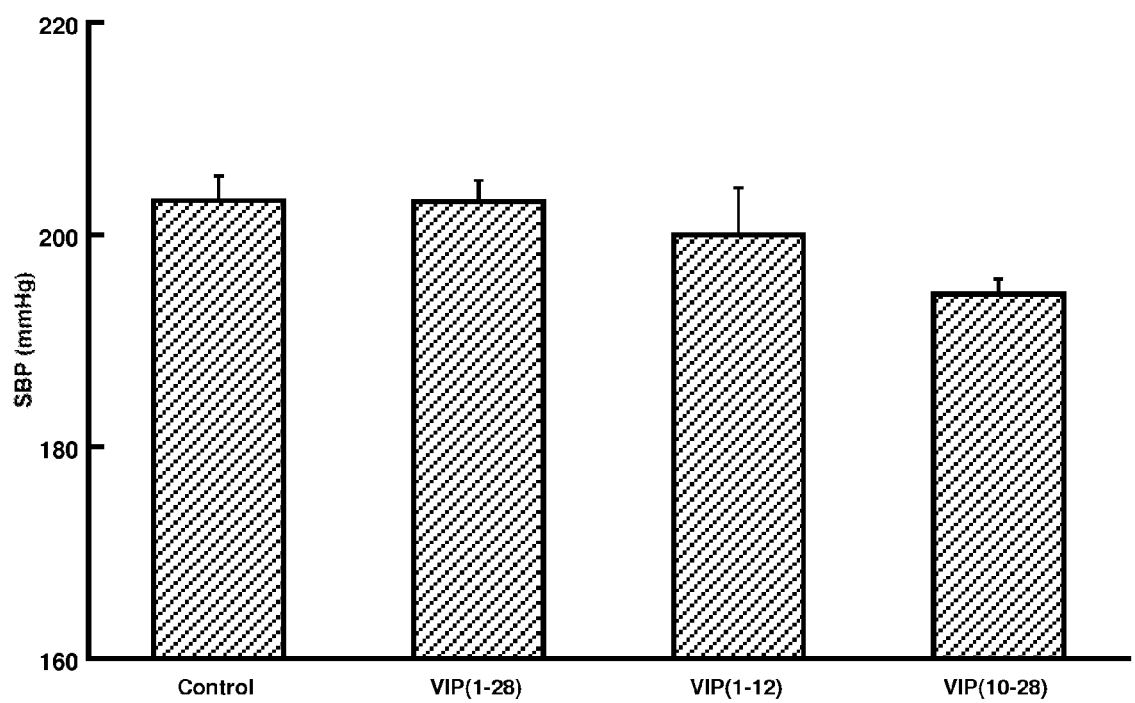
FIG. 9: Systolic blood pressure (SBP) in SHR after 4 weeks on a high salt diet and treated with VIP(1-28) (SEQ ID NO: 1), VIP(1-12) (SEQ ID NO: 91), and VIP(10-28) (SEQ ID NO: 92) or control. All peptides were infused at a dose of 5 pmol/kg/min for 4 weeks.

FIG. 6 illustrates to some extent the difficulty in predicting VIP fragment activity from structure. VIP(4-16) (SEQ ID NO: 35) is less efficacious than either VIP(4-12) (SEQ ID NO: 31), which has 4AA less, or VIP(4-20) (SEQ ID NO: 39), which is 4AA longer. VIP(6-28) (SEQ ID NO: 84) was disclosed in PCT/AU2005/000835 as being effective for preventing myocardial fibrosis.

It is to be appreciated that other embodiments and variants of the compositions, methods and uses of the invention, in keeping with the teaching and the spirit of the invention described, are contemplated and that these are within the scope of the invention.

TABLE 1

VIP fragments and amino acid sequences (native VIP included for reference)

| Amino acid position No. and SEQ ID NO | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| VIP (SEQ ID NO: 1) | His | Ser | Asp | Ala | Val | Phe | Thr | Asp | Asn | Tyr | Thr | Arg | Leu | Arg | Lys | Gln | Met | Ala |
| VIP 11-17 (SEQ ID NO: 2) | | | | | | | | | | | Thr | Arg | Leu | Arg | Lys | Gln | Met | |
| VIP 13-20 (SEQ ID NO: 3) | | | | | | | | | | | | | Leu | Arg | Lys | Gln | Met | Ala |
| VIP 7-27 (SEQ ID NO: 4) | | | | | | | Thr | Asp | Asn | Tyr | Thr | Arg | Leu | Arg | Lys | Gln | Met | Ala |
| VIP 1-27 (SEQ ID NO: 5) | His | Ser | Asp | Ala | Val | Phe | Thr | Asp | Asn | Tyr | Thr | Arg | Leu | Arg | Lys | Gln | Met | Ala |
| VIP 1-26 (SEQ ID NO: 6) | His | Ser | Asp | Ala | Val | Phe | Thr | Asp | Asn | Tyr | Thr | Arg | Leu | Arg | Lys | Gln | Met | Ala |
| VIP 1-23 (SEQ ID NO: 7) | His | Ser | Asp | ala | Val | Phe | Thr | Asp | Asn | Tyr | Thr | Arg | Leu | Arg | Lys | Gln | Met | Ala |
| VIP 1-22 (SEQ ID NO: 8) | His | Ser | Asp | Ala | Val | Phe | Thr | Asp | Asn | Tyr | Thr | Arg | Leu | Arg | Lys | Gln | Met | Ala |
| VIP 1-21 (SEQ ID NO: 9) | His | Ser | Asp | Ala | Val | Phe | Thr | Asp | Asn | Tyr | Thr | Arg | Leu | Arg | Lys | Gln | Met | Ala |
| VIP 1-18 (SEQ ID NO: 10) | His | Ser | Asp | Ala | Val | Phe | Thr | Asp | Asn | Tyr | Thr | Arg | Leu | Arg | Lys | Gln | Met | Ala |
| VIP 1-14 (SEQ ID NO: 11) | His | Ser | Asp | Ala | Val | Phe | Thr | Asp | Asn | Tyr | Thr | Arg | Leu | Arg | | | | |
| VIP 1-11 (SEQ ID NO: 12) | His | Ser | Asp | Ala | Val | Phe | Thr | Asp | Asn | Tyr | Thr | | | | | | | |
| VIP 1-10 (SEQ ID NO: 13) | His | Ser | Asp | Ala | Val | Phe | Thr | Asp | Asn | Tyr | | | | | | | | |
| VIP 1-6 (SEQ ID NO: 14) | His | Ser | Asp | Ala | Val | Phe | | | | | | | | | | | | |
| VIP 9-18 (SEQ ID NO: 15) | | | | | | | | | Asn | Tyr | Thr | Arg | Leu | Arg | Lys | Gln | Met | Ala |
| VIP 15-28 (SEQ ID NO: 16) | | | | | | | | | | | | | | | Lys | Gln | Met | Ala |
| VIP 11-28 (SEQ ID NO: 17) | | | | | | | | | | | Thr | Arg | Leu | Arg | Lys | Gln | Met | Ala |
| VIP 4-28 (SEQ ID NO: 18) | | | | Ala | Val | Phe | Thr | Asp | Asn | Tyr | Thr | Arg | Leu | Arg | Lys | Gln | Met | Ala |
| VIP 2-28 (SEQ ID NO: 19) | | Ser | Asp | Ala | Val | Phe | Thr | Asp | Asn | Tyr | Thr | Arg | Leu | Arg | Lys | Gln | Met | Ala |
| VIP 16-20 (SEQ ID NO: 20) | | | | | | | | | | | | | | | | Gln | Met | Ala |
| VIP 16-19 (SEQ ID NO: 21) | | | | | | | | | | | | | | | | Gln | Met | Ala |
| VIP 17-25 (SEQ ID NO: 22) | | | | | | | | | | | | | | | | | Met | Ala |
| VIP 14-22 (SEQ ID NO: 23) | | | | | | | | | | | | | | Arg | Lys | Gln | Met | Ala |
| VIP 15-28 (SEQ ID NO: 89) | | | | | | | | | | | | | | | Lys | Gln | Met | Ala |
| VIP 15-21 (SEQ ID NO: 24) | | | | | | | | | | | | | | | Lys | Gln | Met | Ala |
| VIP 18-28 (SEQ ID NO: 25) | | | | | | | | | | | | | | | | | | Ala |
| VIP 19-28 (SEQ ID NO: 26) | | | | | | | | | | | | | | | | | | |
| VIP 21-28 (SEQ ID NO: 27) | | | | | | | | | | | | | | | | | | |
| VIP 22-28 (SEQ ID NO: 28) | | | | | | | | | | | | | | | | | | |

TABLE 1-continued

VIP fragments and amino acid sequences (native VIP included for reference)

| | | |
|---|---|---|
| VIP 4-10 (SEQ ID NO: 29) | Ala | Val Phe Thr Asp Asn Tyr |
| VIP 4-11 (SEQ ID NO: 30) | Ala | Val Phe Thr Asp Asn Tyr Thr |
| VIP 4-12 (SEQ ID NO: 31) | Ala | Val Phe Thr Asp Asn Tyr Thr Arg |
| VIP 4-13 (SEQ ID NO: 32) | Ala | Val Phe Thr Asp Asn Tyr Thr Arg Leu |
| VIP 4-14 (SEQ ID NO: 33) | Ala | Val Phe Thr Asp Asn Tyr Thr Arg Leu Arg |
| VIP 4-15 (SEQ ID NO: 34) | Ala | Val Phe Thr Asp Asn Tyr Thr Arg Leu Arg Lys |
| VIP 4-16 (SEQ ID NO: 35) | Ala | Val Phe Thr Asp Asn Tyr Thr Arg Leu Arg Lys Gln |
| VIP 4-17 (SEQ ID NO: 361) | Ala | Val Phe Thr Asp Asn Tyr Thr Arg Leu Arg Lys Gln Met |
| VIP 4-18 (SEQ ID NO: 37) | Ala | Val Phe Thr Asp Asn Tyr Thr Arg Leu Arg Lys Gln Met Ala |
| VIP 4-19 (SEQ ID NO: 38) | Ala | Val Phe Thr Asp Asn Tyr Thr Arg Leu Arg Lys Gln Met Ala |
| VIP 4-20 (SEQ ID NO: 39) | Ala | Val Phe Thr Asp Asn Tyr Thr Arg Leu Arg Lys Gln Met Ala |
| VIP 4-21 (SEQ ID NO: 40) | Ala | Val Phe Thr Asp Asn Tyr Thr Arg Leu Arg Lys Gln Met Ala |
| VIP 4-22 (SEQ ID NO: 41) | Ala | Val Phe Thr Asp Asn Tyr Thr Arg Leu Arg Lys Gln Met Ala |
| VIP 4-23 (SEQ ID NO: 42) | Ala | Val Phe Thr Asp Asn Tyr Thr Arg Leu Arg Lys Gln Met Ala |
| VIP 4-24 (SEQ ID NO: 43) | Ala | Val Phe Thr Asp Asn Tyr Thr Arg Leu Arg Lys Gln Met Ala |
| VIP 4-25 (SEQ ID NO: 44) | Ala | Val Phe Thr Asp Asn Tyr Thr Arg Leu Arg Lys Gln Met Ala |
| VIP 4-26 (SEQ ID NO: 45) | Ala | Val Phe Thr Asp Asn Tyr Thr Arg Leu Arg Lys Gln Met Ala |
| VIP 4-27 (SEQ ID NO: 46) | Ala | Val Phe Thr Asp Asn Tyr Thr Arg Leu Arg Lys Gln Met Ala |
| VIP 4-28 (SEQ ID NO: 90) | Ala | Val Phe Thr Asp Asn Tyr Thr Arg Leu Arg Lys Gln Met Ala |
| VIP 5-10 (SEQ ID NO: 47) | | Val Phe Thr Asp Asn Tyr |
| VIP 5-11 (SEQ ID NO: 48) | | Val Phe Thr Asp Asn Tyr Thr |
| VIP 5-12 (SEQ ID NO: 49) | | Val Phe Thr Asp Asn Tyr Thr Arg |
| VIP 5-13 (SEQ ID NO: 50) | | Val Phe Thr Asp Asn Tyr Thr Arg Leu |
| VIP 5-14 (SEQ ID NO: 51) | | Val Phe Thr Asp Asn Tyr Thr Arg Leu Arg |
| VIP 5-15 (SEQ ID NO: 52) | | Val Phe Thr Asp Asn Tyr Thr Arg Leu Arg Lys |
| VIP 5-16 (SEQ ID NO: 53) | | Val Phe Thr Asp Asn Tyr Thr Arg Leu Arg Lys Gln |
| VIP 5-17 (SEQ ID NO: 54) | | Val Phe Thr Asp Asn Tyr Thr Arg Leu Arg Lys Gln Met |
| VIP 5-18 (SEQ ID NO: 55) | | Val Phe Thr Asp Asn Tyr Thr Arg Leu Arg Lys Gln Met Ala |
| VIP 5-19 (SEQ ID NO: 56) | | Val Phe Thr Asp Asn Tyr Thr Arg Leu Arg Lys Gln Met Ala |
| VIP 5-20 (SEQ ID NO: 57) | | Val Phe Thr Asp Asn Tyr Thr Arg Leu Arg Lys Gln Met Ala |
| VIP 5-21 (SEQ ID NO: 58) | | Val Phe Thr Asp Asn Tyr Thr Arg Leu Arg Lys Gln Met Ala |
| VIP 5-22 (SEQ ID NO: 59) | | Val Phe Thr Asp Asn Tyr Thr Arg Leu Arg Lys Gln Met Ala |
| VIP 5-23 (SEQ ID NO: 60) | | Val Phe Thr Asp Asn Tyr Thr Arg Leu Arg Lys Gln Met Ala |
| VIP 5-24 (SEQ ID NO: 61) | | Val Phe Thr Asp Asn Tyr Thr Arg Leu Arg Lys Gln Met Ala |
| VIP 5-25 (SEQ ID NO: 62) | | Val Phe Thr Asp Asn Tyr Thr Arg Leu Arg Lys Gln Met Ala |
| VIP 5-26 (SEQ ID NO: 63) | | Val Phe Thr Asp Asn Tyr Thr Arg Leu Arg Lys Gln Met Ala |
| VIP 5-27 (SEQ ID NO: 64) | | Val Phe Thr Asp Asn Tyr Thr Arg Leu Arg Lys Gln Met Ala |
| VIP 5-28 (SEQ ID NO: 65) | | Val Phe Thr Asp Asn Tyr Thr Arg Leu Arg Lys Gln Met Ala |
| VIP 6-10 (SEQ ID NO: 66) | | Phe Thr Asp Asn Tyr |

TABLE 1-continued

VIP fragments and amino acid sequences (native VIP included for reference)

| | |
|---|---|
| VIP 6-11 (SEQ ID NO: 67) | Phe Thr Asp Asn Tyr Thr |
| VIP 6-12 (SEQ ID NO: 68) | Phe Thr Asp Asn Tyr Thr Arg |
| VIP 6-13 (SEQ ID NO: 69) | Phe Thr Asp Asn Tyr Thr Arg Leu |
| VIP 6-14 (SEQ ID NO: 70) | Phe Thr Asp Asn Tyr Thr Arg Leu Arg |
| VIP 6-15 (SEQ ID NO: 71) | Phe Thr Asp Asn Tyr Thr Arg Leu Arg Lys |
| VIP 6-16 (SEQ ID NO: 72) | Phe Thr Asp Asn Tyr Thr Arg Leu Arg Lys Gln |
| VIP 6-17 (SEQ ID NO: 73) | Phe Thr Asp Asn Tyr Thr Arg Leu Arg Lys Gln Met |
| VIP 6-18 (SEQ ID NO: 74) | Phe Thr Asp Asn Tyr Thr Arg Leu Arg Lys Gln Met Ala |
| VIP 6-19 (SEQ ID NO: 75) | Phe Thr Asp Asn Tyr Thr Arg Leu Arg Lys Gln Met Ala |
| VIP 6-20 (SEQ ID NO: 76) | Phe Thr Asp Asn Tyr Thr Arg Leu Arg Lys Gln Met Ala |
| VIP 6-21 (SEQ ID NO: 77) | Phe Thr Asp Asn Tyr Thr Arg Leu Arg Lys Gln Met Ala |
| VIP 6-22 (SEQ ID NO: 78) | Phe Thr Asp Asn Tyr Thr Arg Leu Arg Lys Gln Met Ala |
| VIP 6-23 (SEQ ID NO: 79) | Phe Thr Asp Asn Tyr Thr Arg Leu Arg Lys Gln Met Ala |
| VIP 6-24 (SEQ ID NO: 80) | Phe Thr Asp Asn Tyr Thr Arg Leu Arg Lys Gln Met Ala |
| VIP 6-25 (SEQ ID NO: 81) | Phe Thr Asp Asn Tyr Thr Arg Leu Arg Lys Gln Met Ala |
| VIP 6-26 (SEQ ID NO: 82) | Phe Thr Asp Asn Tyr Thr Arg Leu Arg Lys Gln Met Ala |
| VIP 6-27 (SEQ ID NO: 83) | Phe Thr Asp Asn Tyr Thr Arg Leu Arg Lys Gln Met Ala |
| VIP 6-28 (SEQ ID NO: 84) | Phe Thr Asp Asn Tyr Thr Arg Leu Arg Lys Gln Met Ala |
| VIP 16-25 (SEQ ID NO: 85) | Gln Met Ala |
| VIP 16-26 (SEQ ID NO: 86) | Gln Met Ala |
| VIP 16-27 (SEQ ID NO: 87) | Gln Met Ala |
| VIP 16-28 (SEQ ID NO: 88) | Gln Met Ala |

| Amino acid position No. and SEQ ID NO | 19 | 20 | 21 | 22 | 23 | 24 | 25 | 26 | 27 | 28 | 29 | 30 | 31 | 32 |
|---|---|---|---|---|---|---|---|---|---|---|---|---|---|---|
| VIP (SEQ ID NO: 1) | Val | Lys | Lys | Tyr | Leu | Asn | Ser | Ile | Leu | Asn | | | | |
| VIP 11-17 (SEQ ID NO: 2) | | | | | | | | | | | | | | |
| VIP 13-20 (SEQ ID NO: 3) | Val | Lys | | | | | | | | | | | | |
| VIP 7-27 (SEQ ID NO: 4) | Val | Lys | Lys | Tyr | Leu | Asn | Ser | Ile | Leu | Asn | | | | |
| VIP 1-27 (SEQ ID NO: 5) | Val | Lys | Lys | Tyr | Leu | Asn | Ser | Ile | Leu | | | | | |
| VIP 1-26 (SEQ ID NO: 6) | Val | Lys | Lys | Tyr | Leu | Asn | Ser | Ile | | | | | | |
| VIP 1-23 (SEQ ID NO: 7) | Val | Lys | Lys | Tyr | Leu | | | | | | | | | |
| VIP 1-22 (SEQ ID NO: 8) | Val | Lys | Lys | Tyr | | | | | | | | | | |
| VIP 1-21 (SEQ ID NO: 9) | Val | Lys | Lys | | | | | | | | | | | |
| VIP 1-18 (SEQ ID NO: 10) | | | | | | | | | | | | | | |
| VIP 1-14 (SEQ ID NO: 11) | | | | | | | | | | | | | | |
| VIP 1-11 (SEQ ID NO: 12) | | | | | | | | | | | | | | |
| VIP 1-10 (SEQ ID NO: 13) | | | | | | | | | | | | | | |
| VIP 1-6 (SEQ ID NO: 14) | | | | | | | | | | | | | | |
| VIP 9-18 (SEQ ID NO: 15) | | | | | | | | | | | | | | |
| VIP 15-28 (SEQ ID NO: 16) | Val | Lys | Lys | Tyr | Leu | Asn | Ser | Ile | Leu | Asn | | | | |

TABLE 1-continued

VIP fragments and amino acid sequences (native VIP included for reference)

| | |
|---|---|
| VIP 11-28 (SEQ ID NO: 17) | Val Lys Lys Tyr Leu Asn Ser Ile Leu Asn |
| VIP 4-28 (SEQ ID NO: 18) | Val Lys Lys Tyr Leu Asn Ser Ile Leu Asn |
| VIP 2-28 (SEQ ID NO: 19) | Val Lys Lys Tyr Leu Asn Ser Ile Leu Asn |
| VIP 16-20 (SEQ ID NO: 20) | Val Lys |
| VIP 16-19 (SEQ ID NO: 21) | Val |
| VIP 17-25 (SEQ ID NO: 22) | Val Lys Lys Tyr Leu Asn Ser |
| VIP 14-22 (SEQ ID NO: 23) | Val Lys Lys Tyr |
| VIP 15-28 (SEQ ID NO: 89) | Val Lys Lys Tyr Leu Asn Ser Ile Leu Asn |
| VIP 15-21 (SEQ ID NO: 24) | Val Lys Lys |
| VIP 18-28 (SEQ ID NO: 25) | Val Lys Lys Tyr Leu Asn Ser Ile Leu Asn |
| VIP 19-28 (SEQ ID NO: 26) | Val Lys Lys Tyr Leu Asn Ser Ile Leu Asn |
| VIP 21-28 (SEQ ID NO: 27) | Lys Tyr Leu Asn Ser Ile Leu Asn |
| VIP 22-28 (SEQ ID NO: 28) | Tyr Leu Asn Ser Ile Leu Asn |
| VIP 4-10 (SEQ ID NO: 29) | |
| VIP 4-11 (SEQ ID NO: 30) | |
| VIP 4-12 (SEQ ID NO: 31) | |
| VIP 4-13 (SEQ ID NO: 32) | |
| VIP 4-14 (SEQ ID NO: 33) | |
| VIP 4-15 (SEQ ID NO: 34) | |
| VIP 4-16 (SEQ ID NO: 35) | |
| VIP 4-17 (SEQ ID NO: 361) | |
| VIP 4-18 (SEQ ID NO: 37) | |
| VIP 4-19 (SEQ ID NO: 38) | Val |
| VIP 4-20 (SEQ ID NO: 39) | Val Lys |
| VIP 4-21 (SEQ ID NO: 40) | Val Lys Lys |
| VIP 4-22 (SEQ ID NO: 41) | Val Lys Lys Tyr |
| VIP 4-23 (SEQ ID NO: 42) | Val Lys Lys Tyr Leu |
| VIP 4-24 (SEQ ID NO: 43) | Val Lys Lys Tyr Leu Asn |
| VIP 4-25 (SEQ ID NO: 44) | Val Lys Lys Tyr Leu Asn Ser |
| VIP 4-26 (SEQ ID NO: 45) | Val Lys Lys Tyr Leu Asn Ser Ile |
| VIP 4-27 (SEQ ID NO: 46) | Val Lys Lys Tyr Leu Asn Ser Ile Leu |
| VIP 4-28 (SEQ ID NO: 90) | Val Lys Lys Tyr Leu Asn Ser Ile Leu Asn |
| VIP 5-10 (SEQ ID NO: 47) | |
| VIP 5-11 (SEQ ID NO: 48) | |
| VIP 5-12 (SEQ ID NO: 49) | |
| VIP 5-13 (SEQ ID NO: 50) | |
| VIP 5-14 (SEQ ID NO: 51) | |
| VIP 5-15 (SEQ ID NO: 52) | |
| VIP 5-16 (SEQ ID NO: 53) | |

TABLE 1-continued

VIP fragments and amino acid sequences (native VIP included for reference)

| | |
|---|---|
| VIP 5-17 (SEQ ID NO: 54) | |
| VIP 5-18 (SEQ ID NO: 55) | |
| VIP 5-19 (SEQ ID NO: 56) | Val |
| VIP 5-20 (SEQ ID NO: 57) | Val Lys |
| VIP 5-21 (SEQ ID NO: 58) | Val Lys Lys |
| VIP 5-22 (SEQ ID NO: 59) | Val Lys Lys Tyr |
| VIP 5-23 (SEQ ID NO: 60) | Val Lys Lys Tyr Leu |
| VIP 5-24 (SEQ ID NO: 61) | Val Lys Lys Tyr Leu Asn |
| VIP 5-25 (SEQ ID NO: 62) | Val Lys Lys Tyr Leu Asn Ser |
| VIP 5-26 (SEQ ID NO: 63) | Val Lys Lys Tyr Leu Asn Ser Ile |
| VIP 5-27 (SEQ ID NO: 64) | Val Lys Lys Tyr Leu Asn Ser Ile Leu |
| VIP 5-28 (SEQ ID NO: 65) | Val Lys Lys Tyr Leu Asn Ser Ile Leu Asn |
| VIP 6-10 (SEQ ID NO: 66) | |
| VIP 6-11 (SEQ ID NO: 67) | |
| VIP 6-12 (SEQ ID NO: 68) | |
| VIP 6-13 (SEQ ID NO: 69) | |
| VIP 6-14 (SEQ ID NO: 70) | |
| VIP 6-15 (SEQ ID NO: 71) | |
| VIP 6-16 (SEQ ID NO: 72) | |
| VIP 6-17 (SEQ ID NO: 73) | |
| VIP 6-18 (SEQ ID NO: 74) | |
| VIP 6-19 (SEQ ID NO: 75) | Val |
| VIP 6-20 (SEQ ID NO: 76) | Val Lys |
| VIP 6-21 (SEQ ID NO: 77) | Val Lys Lys |
| VIP 6-22 (SEQ ID NO: 78) | Val Lys Lys Tyr |
| VIP 6-23 (SEQ ID NO: 79) | Val Lys Lys Tyr Leu |
| VIP 6-24 (SEQ ID NO: 80) | Val Lys Lys Tyr Leu Asn |
| VIP 6-25 (SEQ ID NO: 81) | Val Lys Lys Tyr Leu Asn Ser |
| VIP 6-26 (SEQ ID NO: 82) | Val Lys Lys Tyr Leu Asn Ser Ile |
| VIP 6-27 (SEQ ID NO: 83) | Val Lys Lys Tyr Leu Asn Ser Ile Leu |
| VIP 6-28 (SEQ ID NO: 84) | Val Lys Lys Tyr Leu Asn Ser Ile Leu Asn |
| VIP 16-25 (SEQ ID NO: 85) | Val Lys Lys Tyr Leu Asn Ser |
| VIP 16-26 (SEQ ID NO: 86) | Val Lys Lys Tyr Leu Asn Ser Ile |
| VIP 16-27 (SEQ ID NO: 87) | Val Lys Lys Tyr Leu Asn Ser Ile Leu |
| VIP 16-28 (SEQ ID NO: 88) | Val Lys Lys Tyr Leu Asn Ser Ile Leu Asn |

What is claimed is:

1. A method of therapeutic treatment of myocardial fibrosis, or an associated condition, in a subject, wherein the method comprises administering to a subject in need thereof a composition comprising one or more VIP fragments selected from the group consisting of: VIP(6-10) (SEQ ID NO: 66), VIP(6-12) (SEQ ID NO: 68), VIP(6-16) (SEQ ID NO: 72), VIP(6-20) (SEQ ID NO: 76), VIP(6-24) (SEQ ID NO: 80), and conservative substitutions thereof that do not alter the biological activity of the fragment, wherein the associated condition is selected from the group consisting of: hypertension, diabetes, myocarditis, ischaemic heart disease, left ventricular hypertrophy, diastolic dysfunction, cardiomyopathy, left ventricular dysfunction, congestive cardiac failure, Conn's Syndrome and Phaeochromocytoma.

2. The method of claim 1, wherein the method slows the progression of myocardial fibrosis.

3. The method of claim 1, wherein the method reduces the degree of myocardial fibrosis.

4. The method of claim 1, wherein the method treats myocardial fibrosis by inhibiting or reducing the production of fibrotic mediators, reducing collagen formation, enhancing collagen degradation, or lowering blood pressure.

5. The method of claim 1 wherein the associated condition is hypertension.

6. A method of treating a condition associated with myocardial fibrosis in a subject with myocardial fibrosis, wherein the condition is selected from the group consisting of: hypertension, diabetes, myocarditis, ischaemic heart disease, left ventricular hypertrophy, diastolic dysfunction, cardiomyopathy, left ventricular dysfunction, congestive cardiac failure, Conn's Syndrome and Phaeochromocytoma, wherein the method comprises administering to a subject in need thereof a composition according to claim comprising one or more VIP fragments selected from the group consisting of: VIP(6-10) (SEQ ID NO: 66), VIP(6-12) (SEQ ID NO: 68), VIP(6-16) (SEQ ID NO: 72), VIP(6-20) (SEQ ID NO: 76), VIP(6-24) (SEQ ID NO: 80), and conservative substitutions thereof that do not alter the biological activity of the fragment.

7. The method of claim 6, wherein the condition gives rise to generation of profibrotic mediators or predisposes the subject to myocardial fibrosis.

8. The method of claim 6, wherein the condition is hypertension or diabetes.

9. The method of claim 6, wherein the condition is hypertension.

10. A method of therapeutic treatment of myocardial fibrosis in a subject by reducing hypertension, wherein the method comprises administering to a subject in need thereof a composition comprising one or more VIP fragments selected from the group consisting of: VIP(6-10) (SEQ ID NO: 66), VIP(6-12) (SEQ ID NO: 68), VIP(6-16) (SEQ ID NO: 72), VIP(6-20) (SEQ ID NO: 76), VIP(6-24) (SEQ ID NO: 80), and conservative substitutions thereof that do not alter the biological activity of the fragment.

11. The method of claim 10, wherein the method slows the progression of myocardial fibrosis.

12. The method of claim 10, wherein the method reduces the degree of myocardial fibrosis.

13. A method of lowering blood pressure in a subject, wherein the method comprises administering to a subject in need thereof a composition comprising one or more VIP fragments selected from the group consisting of: VIP(6-10) (SEQ ID NO: 66), VIP(6-12) (SEQ ID NO: 68), VIP(6-16) (SEQ ID NO: 72), VIP(6-20) (SEQ ID NO: 76), VIP(6-24) (SEQ ID NO: 80), and conservative substitutions thereof that do not alter the biological activity of the fragment.

* * * * *

SEQUENCE LISTING

<160> NUMBER OF SEQ ID NOS: 94

<210> SEQ ID NO 1
<211> LENGTH: 28
<212> TYPE: PRT
<213> ORGANISM: Homo sapiens

<400> SEQUENCE: 1

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 2
<211> LENGTH: 7
<212> TYPE: PRT
<213> ORGANISM: Homo sapiens

<400> SEQUENCE: 2

Thr Arg Leu Arg Lys Gln Met
1               5

<210> SEQ ID NO 3
<211> LENGTH: 8
<212> TYPE: PRT
<213> ORGANISM: Homo sapiens

<400> SEQUENCE: 3

Leu Arg Lys Gln Met Ala Val Lys
1               5

<210> SEQ ID NO 4
<211> LENGTH: 22
<212> TYPE: PRT
<213> ORGANISM: Homo sapiens

<400> SEQUENCE: 4

Thr Asp Asn Tyr Thr Arg Leu Arg Lys Gln Met Ala Val Lys Lys Tyr
1               5                   10                  15

Leu Asn Ser Ile Leu Asn
            20

<210> SEQ ID NO 5
<211> LENGTH: 27
<212> TYPE: PRT
<213> ORGANISM: Homo sapiens

<400> SEQUENCE: 5

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu
            20                  25

<210> SEQ ID NO 6
<211> LENGTH: 26
<212> TYPE: PRT
<213> ORGANISM: Homo sapiens

<400> SEQUENCE: 6

His Ser Asp Ala Val Phe Thr Asp Asn Tyr Thr Arg Leu Arg Lys Gln
1               5                   10                  15

Met Ala Val Lys Lys Tyr Leu Asn Ser Ile
            20                  25

```
<210> SEQ ID NO 7
<211> LENGTH: 23
<212> TYPE: PRT
<213> ORGANISM: Homo sapiens

<400> SEQUENCE: 7

His Ser Asp Ala Val Phe Thr Asp Asn Tyr Thr Arg Leu Arg Lys Gln
1               5                   10                  15

Met Ala Val Lys Lys Tyr Leu
            20

<210> SEQ ID NO 8
<211> LENGTH: 22
<212> TYPE: PRT
<213> ORGANISM: Homo sapiens

<400> SEQUENCE: 8

His Ser Asp Ala Val Phe Thr Asp Asn Tyr Thr Arg Leu Arg Lys Gln
1               5                   10                  15

Met Ala Val Lys Lys Tyr
            20

<210> SEQ ID NO 9
<211> LENGTH: 21
<212> TYPE: PRT
<213> ORGANISM: Homo sapiens

<400> SEQUENCE: 9

His Ser Asp Ala Val Phe Thr Asp Asn Tyr Thr Arg Leu Arg Lys Gln
1               5                   10                  15

Met Ala Val Lys Lys
            20

<210> SEQ ID NO 10
<211> LENGTH: 18
<212> TYPE: PRT
<213> ORGANISM: Homo sapiens

<400> SEQUENCE: 10

His Ser Asp Ala Val Phe Thr Asp Asn Tyr Thr Arg Leu Arg Lys Gln
1               5                   10                  15

Met Ala

<210> SEQ ID NO 11
<211> LENGTH: 14
<212> TYPE: PRT
<213> ORGANISM: Homo sapiens

<400> SEQUENCE: 11

His Ser Asp Ala Val Phe Thr Asp Asn Tyr Thr Arg Leu Arg
1               5                   10

<210> SEQ ID NO 12
<211> LENGTH: 11
<212> TYPE: PRT
<213> ORGANISM: Homo sapiens

<400> SEQUENCE: 12

His Ser Asp Ala Val Phe Thr Asp Asn Tyr Thr
1               5                   10
```

-continued

```
<210> SEQ ID NO 13
<211> LENGTH: 10
<212> TYPE: PRT
<213> ORGANISM: Homo sapiens

<400> SEQUENCE: 13

His Ser Asp Ala Val Phe Thr Asp Asn Tyr
1               5                  10

<210> SEQ ID NO 14
<211> LENGTH: 6
<212> TYPE: PRT
<213> ORGANISM: Homo sapiens

<400> SEQUENCE: 14

His Ser Asp Ala Val Phe
1               5

<210> SEQ ID NO 15
<211> LENGTH: 10
<212> TYPE: PRT
<213> ORGANISM: Homo sapiens

<400> SEQUENCE: 15

Asn Tyr Thr Arg Leu Arg Lys Gln Met Ala
1               5                  10

<210> SEQ ID NO 16
<211> LENGTH: 14
<212> TYPE: PRT
<213> ORGANISM: Homo sapiens

<400> SEQUENCE: 16

Lys Gln Met Ala Val Lys Lys Tyr Leu Asn Ser Ile Leu Asn
1               5                  10

<210> SEQ ID NO 17
<211> LENGTH: 18
<212> TYPE: PRT
<213> ORGANISM: Homo sapiens

<400> SEQUENCE: 17

Thr Arg Leu Arg Lys Gln Met Ala Val Lys Lys Tyr Leu Asn Ser Ile
1               5                  10                  15

Leu Asn

<210> SEQ ID NO 18
<211> LENGTH: 25
<212> TYPE: PRT
<213> ORGANISM: Homo sapiens

<400> SEQUENCE: 18

Ala Val Phe Thr Asp Asn Tyr Thr Arg Leu Arg Lys Gln Met Ala Val
1               5                  10                  15

Lys Lys Tyr Leu Asn Ser Ile Leu Asn
            20                  25

<210> SEQ ID NO 19
<211> LENGTH: 27
<212> TYPE: PRT
<213> ORGANISM: Homo sapiens

<400> SEQUENCE: 19

Ser Asp Ala Val Phe Thr Asp Asn Tyr Thr Arg Leu Arg Lys Gln Met
```

```
                1               5                  10                  15
Ala Val Lys Lys Tyr Leu Asn Ser Ile Leu Asn
            20                  25

<210> SEQ ID NO 20
<211> LENGTH: 5
<212> TYPE: PRT
<213> ORGANISM: Homo sapiens

<400> SEQUENCE: 20

Gln Met Ala Val Lys
1               5

<210> SEQ ID NO 21
<211> LENGTH: 4
<212> TYPE: PRT
<213> ORGANISM: Homo sapiens

<400> SEQUENCE: 21

Gln Met Ala Val
1

<210> SEQ ID NO 22
<211> LENGTH: 9
<212> TYPE: PRT
<213> ORGANISM: Homo sapiens

<400> SEQUENCE: 22

Met Ala Val Lys Lys Tyr Leu Asn Ser
1               5

<210> SEQ ID NO 23
<211> LENGTH: 9
<212> TYPE: PRT
<213> ORGANISM: Homo sapiens

<400> SEQUENCE: 23

Arg Lys Gln Met Ala Val Lys Lys Tyr
1               5

<210> SEQ ID NO 24
<211> LENGTH: 7
<212> TYPE: PRT
<213> ORGANISM: Homo sapiens

<400> SEQUENCE: 24

Lys Gln Met Ala Val Lys Lys
1               5

<210> SEQ ID NO 25
<211> LENGTH: 11
<212> TYPE: PRT
<213> ORGANISM: Homo sapiens

<400> SEQUENCE: 25

Ala Val Lys Lys Tyr Leu Asn Ser Ile Leu Asn
1               5                  10

<210> SEQ ID NO 26
<211> LENGTH: 10
<212> TYPE: PRT
<213> ORGANISM: Homo sapiens

<400> SEQUENCE: 26
```

Val Lys Lys Tyr Leu Asn Ser Ile Leu Asn
1               5                   10

<210> SEQ ID NO 27
<211> LENGTH: 8
<212> TYPE: PRT
<213> ORGANISM: Homo sapiens

<400> SEQUENCE: 27

Lys Tyr Leu Asn Ser Ile Leu Asn
1               5

<210> SEQ ID NO 28
<211> LENGTH: 7
<212> TYPE: PRT
<213> ORGANISM: Homo sapiens

<400> SEQUENCE: 28

Tyr Leu Asn Ser Ile Leu Asn
1               5

<210> SEQ ID NO 29
<211> LENGTH: 7
<212> TYPE: PRT
<213> ORGANISM: Homo sapiens

<400> SEQUENCE: 29

Ala Val Phe Thr Asp Asn Tyr
1               5

<210> SEQ ID NO 30
<211> LENGTH: 8
<212> TYPE: PRT
<213> ORGANISM: Homo sapiens

<400> SEQUENCE: 30

Ala Val Phe Thr Asp Asn Tyr Thr
1               5

<210> SEQ ID NO 31
<211> LENGTH: 9
<212> TYPE: PRT
<213> ORGANISM: Homo sapiens

<400> SEQUENCE: 31

Ala Val Phe Thr Asp Asn Tyr Thr Arg
1               5

<210> SEQ ID NO 32
<211> LENGTH: 10
<212> TYPE: PRT
<213> ORGANISM: Homo sapiens

<400> SEQUENCE: 32

Ala Val Phe Thr Asp Asn Tyr Thr Arg Leu
1               5                   10

<210> SEQ ID NO 33
<211> LENGTH: 11
<212> TYPE: PRT
<213> ORGANISM: Homo sapiens

<400> SEQUENCE: 33

Ala Val Phe Thr Asp Asn Tyr Thr Arg Leu Arg
1               5                   10

<210> SEQ ID NO 34
<211> LENGTH: 12
<212> TYPE: PRT
<213> ORGANISM: Homo sapiens

<400> SEQUENCE: 34

Ala Val Phe Thr Asp Asn Tyr Thr Arg Leu Arg Lys
1               5                   10

<210> SEQ ID NO 35
<211> LENGTH: 13
<212> TYPE: PRT
<213> ORGANISM: Homo sapiens

<400> SEQUENCE: 35

Ala Val Phe Thr Asp Asn Tyr Thr Arg Leu Arg Lys Gln
1               5                   10

<210> SEQ ID NO 36
<211> LENGTH: 14
<212> TYPE: PRT
<213> ORGANISM: Homo sapiens

<400> SEQUENCE: 36

Ala Val Phe Thr Asp Asn Tyr Thr Arg Leu Arg Lys Gln Met
1               5                   10

<210> SEQ ID NO 37
<211> LENGTH: 15
<212> TYPE: PRT
<213> ORGANISM: Homo sapiens

<400> SEQUENCE: 37

Ala Val Phe Thr Asp Asn Tyr Thr Arg Leu Arg Lys Gln Met Ala
1               5                   10                  15

<210> SEQ ID NO 38
<211> LENGTH: 16
<212> TYPE: PRT
<213> ORGANISM: Homo sapiens

<400> SEQUENCE: 38

Ala Val Phe Thr Asp Asn Tyr Thr Arg Leu Arg Lys Gln Met Ala Val
1               5                   10                  15

<210> SEQ ID NO 39
<211> LENGTH: 17
<212> TYPE: PRT
<213> ORGANISM: Homo sapiens

<400> SEQUENCE: 39

Ala Val Phe Thr Asp Asn Tyr Thr Arg Leu Arg Lys Gln Met Ala Val
1               5                   10                  15

Lys

<210> SEQ ID NO 40
<211> LENGTH: 18
<212> TYPE: PRT
<213> ORGANISM: Homo sapiens

<400> SEQUENCE: 40

Ala Val Phe Thr Asp Asn Tyr Thr Arg Leu Arg Lys Gln Met Ala Val
1               5                   10                  15

Lys Lys

<210> SEQ ID NO 41
<211> LENGTH: 19
<212> TYPE: PRT
<213> ORGANISM: Homo sapiens

<400> SEQUENCE: 41

Ala Val Phe Thr Asp Asn Tyr Thr Arg Leu Arg Lys Gln Met Ala Val
1               5                   10                  15

Lys Lys Tyr

<210> SEQ ID NO 42
<211> LENGTH: 20
<212> TYPE: PRT
<213> ORGANISM: Homo sapiens

<400> SEQUENCE: 42

Ala Val Phe Thr Asp Asn Tyr Thr Arg Leu Arg Lys Gln Met Ala Val
1               5                   10                  15

Lys Lys Tyr Leu
            20

<210> SEQ ID NO 43
<211> LENGTH: 21
<212> TYPE: PRT
<213> ORGANISM: Homo sapiens

<400> SEQUENCE: 43

Ala Val Phe Thr Asp Asn Tyr Thr Arg Leu Arg Lys Gln Met Ala Val
1               5                   10                  15

Lys Lys Tyr Leu Asn
            20

<210> SEQ ID NO 44
<211> LENGTH: 22
<212> TYPE: PRT
<213> ORGANISM: Homo sapiens

<400> SEQUENCE: 44

Ala Val Phe Thr Asp Asn Tyr Thr Arg Leu Arg Lys Gln Met Ala Val
1               5                   10                  15

Lys Lys Tyr Leu Asn Ser
            20

<210> SEQ ID NO 45
<211> LENGTH: 23
<212> TYPE: PRT
<213> ORGANISM: Homo sapiens

<400> SEQUENCE: 45

Ala Val Phe Thr Asp Asn Tyr Thr Arg Leu Arg Lys Gln Met Ala Val
1               5                   10                  15

Lys Lys Tyr Leu Asn Ser Ile
            20

<210> SEQ ID NO 46
<211> LENGTH: 24
<212> TYPE: PRT
<213> ORGANISM: Homo sapiens

<400> SEQUENCE: 46

```
Ala Val Phe Thr Asp Asn Tyr Thr Arg Leu Arg Lys Gln Met Ala Val
1               5                  10                  15

Lys Lys Tyr Leu Asn Ser Ile Leu
            20
```

<210> SEQ ID NO 47
<211> LENGTH: 6
<212> TYPE: PRT
<213> ORGANISM: Homo sapiens

<400> SEQUENCE: 47

```
Val Phe Thr Asp Asn Tyr
1               5
```

<210> SEQ ID NO 48
<211> LENGTH: 7
<212> TYPE: PRT
<213> ORGANISM: Homo sapiens

<400> SEQUENCE: 48

```
Val Phe Thr Asp Asn Tyr Thr
1               5
```

<210> SEQ ID NO 49
<211> LENGTH: 8
<212> TYPE: PRT
<213> ORGANISM: Homo sapiens

<400> SEQUENCE: 49

```
Val Phe Thr Asp Asn Tyr Thr Arg
1               5
```

<210> SEQ ID NO 50
<211> LENGTH: 9
<212> TYPE: PRT
<213> ORGANISM: Homo sapiens

<400> SEQUENCE: 50

```
Val Phe Thr Asp Asn Tyr Thr Arg Leu
1               5
```

<210> SEQ ID NO 51
<211> LENGTH: 10
<212> TYPE: PRT
<213> ORGANISM: Homo sapiens

<400> SEQUENCE: 51

```
Val Phe Thr Asp Asn Tyr Thr Arg Leu Arg
1               5                  10
```

<210> SEQ ID NO 52
<211> LENGTH: 11
<212> TYPE: PRT
<213> ORGANISM: Homo sapiens

<400> SEQUENCE: 52

```
Val Phe Thr Asp Asn Tyr Thr Arg Leu Arg Lys
1               5                  10
```

<210> SEQ ID NO 53
<211> LENGTH: 12
<212> TYPE: PRT
<213> ORGANISM: Homo sapiens

```
<400> SEQUENCE: 53

Val Phe Thr Asp Asn Tyr Thr Arg Leu Arg Lys Gln
1               5                   10

<210> SEQ ID NO 54
<211> LENGTH: 13
<212> TYPE: PRT
<213> ORGANISM: Homo sapiens

<400> SEQUENCE: 54

Val Phe Thr Asp Asn Tyr Thr Arg Leu Arg Lys Gln Met
1               5                   10

<210> SEQ ID NO 55
<211> LENGTH: 14
<212> TYPE: PRT
<213> ORGANISM: Homo sapiens

<400> SEQUENCE: 55

Val Phe Thr Asp Asn Tyr Thr Arg Leu Arg Lys Gln Met Ala
1               5                   10

<210> SEQ ID NO 56
<211> LENGTH: 15
<212> TYPE: PRT
<213> ORGANISM: Homo sapiens

<400> SEQUENCE: 56

Val Phe Thr Asp Asn Tyr Thr Arg Leu Arg Lys Gln Met Ala Val
1               5                   10                  15

<210> SEQ ID NO 57
<211> LENGTH: 16
<212> TYPE: PRT
<213> ORGANISM: Homo sapiens

<400> SEQUENCE: 57

Val Phe Thr Asp Asn Tyr Thr Arg Leu Arg Lys Gln Met Ala Val Lys
1               5                   10                  15

<210> SEQ ID NO 58
<211> LENGTH: 17
<212> TYPE: PRT
<213> ORGANISM: Homo sapiens

<400> SEQUENCE: 58

Val Phe Thr Asp Asn Tyr Thr Arg Leu Arg Lys Gln Met Ala Val Lys
1               5                   10                  15

Lys

<210> SEQ ID NO 59
<211> LENGTH: 18
<212> TYPE: PRT
<213> ORGANISM: Homo sapiens

<400> SEQUENCE: 59

Val Phe Thr Asp Asn Tyr Thr Arg Leu Arg Lys Gln Met Ala Val Lys
1               5                   10                  15

Lys Tyr

<210> SEQ ID NO 60
<211> LENGTH: 19
<212> TYPE: PRT
```

-continued

<213> ORGANISM: Homo sapiens

<400> SEQUENCE: 60

Val Phe Thr Asp Asn Tyr Thr Arg Leu Arg Lys Gln Met Ala Val Lys
1               5                   10                  15

Lys Tyr Leu

<210> SEQ ID NO 61
<211> LENGTH: 20
<212> TYPE: PRT
<213> ORGANISM: Homo sapiens

<400> SEQUENCE: 61

Val Phe Thr Asp Asn Tyr Thr Arg Leu Arg Lys Gln Met Ala Val Lys
1               5                   10                  15

Lys Tyr Leu Asn
            20

<210> SEQ ID NO 62
<211> LENGTH: 21
<212> TYPE: PRT
<213> ORGANISM: Homo sapiens

<400> SEQUENCE: 62

Val Phe Thr Asp Asn Tyr Thr Arg Leu Arg Lys Gln Met Ala Val Lys
1               5                   10                  15

Lys Tyr Leu Asn Ser
            20

<210> SEQ ID NO 63
<211> LENGTH: 22
<212> TYPE: PRT
<213> ORGANISM: Homo sapiens

<400> SEQUENCE: 63

Val Phe Thr Asp Asn Tyr Thr Arg Leu Arg Lys Gln Met Ala Val Lys
1               5                   10                  15

Lys Tyr Leu Asn Ser Ile
            20

<210> SEQ ID NO 64
<211> LENGTH: 23
<212> TYPE: PRT
<213> ORGANISM: Homo sapiens

<400> SEQUENCE: 64

Val Phe Thr Asp Asn Tyr Thr Arg Leu Arg Lys Gln Met Ala Val Lys
1               5                   10                  15

Lys Tyr Leu Asn Ser Ile Leu
            20

<210> SEQ ID NO 65
<211> LENGTH: 24
<212> TYPE: PRT
<213> ORGANISM: Homo sapiens

<400> SEQUENCE: 65

Val Phe Thr Asp Asn Tyr Thr Arg Leu Arg Lys Gln Met Ala Val Lys
1               5                   10                  15

Lys Tyr Leu Asn Ser Ile Leu Asn
            20

```
<210> SEQ ID NO 66
<211> LENGTH: 5
<212> TYPE: PRT
<213> ORGANISM: Homo sapiens

<400> SEQUENCE: 66

Phe Thr Asp Asn Tyr
1               5

<210> SEQ ID NO 67
<211> LENGTH: 6
<212> TYPE: PRT
<213> ORGANISM: Homo sapiens

<400> SEQUENCE: 67

Phe Thr Asp Asn Tyr Thr
1               5

<210> SEQ ID NO 68
<211> LENGTH: 7
<212> TYPE: PRT
<213> ORGANISM: Homo sapiens

<400> SEQUENCE: 68

Phe Thr Asp Asn Tyr Thr Arg
1               5

<210> SEQ ID NO 69
<211> LENGTH: 8
<212> TYPE: PRT
<213> ORGANISM: Homo sapiens

<400> SEQUENCE: 69

Phe Thr Asp Asn Tyr Thr Arg Leu
1               5

<210> SEQ ID NO 70
<211> LENGTH: 9
<212> TYPE: PRT
<213> ORGANISM: Homo sapiens

<400> SEQUENCE: 70

Phe Thr Asp Asn Tyr Thr Arg Leu Arg
1               5

<210> SEQ ID NO 71
<211> LENGTH: 10
<212> TYPE: PRT
<213> ORGANISM: Homo sapiens

<400> SEQUENCE: 71

Phe Thr Asp Asn Tyr Thr Arg Leu Arg Lys
1               5                   10

<210> SEQ ID NO 72
<211> LENGTH: 11
<212> TYPE: PRT
<213> ORGANISM: Homo sapiens

<400> SEQUENCE: 72

Phe Thr Asp Asn Tyr Thr Arg Leu Arg Lys Gln
1               5                   10

<210> SEQ ID NO 73
```

```
<211> LENGTH: 12
<212> TYPE: PRT
<213> ORGANISM: Homo sapiens

<400> SEQUENCE: 73

Phe Thr Asp Asn Tyr Thr Arg Leu Arg Lys Gln Met
1               5                   10

<210> SEQ ID NO 74
<211> LENGTH: 13
<212> TYPE: PRT
<213> ORGANISM: Homo sapiens

<400> SEQUENCE: 74

Phe Thr Asp Asn Tyr Thr Arg Leu Arg Lys Gln Met Ala
1               5                   10

<210> SEQ ID NO 75
<211> LENGTH: 14
<212> TYPE: PRT
<213> ORGANISM: Homo sapiens

<400> SEQUENCE: 75

Phe Thr Asp Asn Tyr Thr Arg Leu Arg Lys Gln Met Ala Val
1               5                   10

<210> SEQ ID NO 76
<211> LENGTH: 15
<212> TYPE: PRT
<213> ORGANISM: Homo sapiens

<400> SEQUENCE: 76

Phe Thr Asp Asn Tyr Thr Arg Leu Arg Lys Gln Met Ala Val Lys
1               5                   10                  15

<210> SEQ ID NO 77
<211> LENGTH: 16
<212> TYPE: PRT
<213> ORGANISM: Homo sapiens

<400> SEQUENCE: 77

Phe Thr Asp Asn Tyr Thr Arg Leu Arg Lys Gln Met Ala Val Lys Lys
1               5                   10                  15

<210> SEQ ID NO 78
<211> LENGTH: 17
<212> TYPE: PRT
<213> ORGANISM: Homo sapiens

<400> SEQUENCE: 78

Phe Thr Asp Asn Tyr Thr Arg Leu Arg Lys Gln Met Ala Val Lys Lys
1               5                   10                  15

Tyr

<210> SEQ ID NO 79
<211> LENGTH: 18
<212> TYPE: PRT
<213> ORGANISM: Homo sapiens

<400> SEQUENCE: 79

Phe Thr Asp Asn Tyr Thr Arg Leu Arg Lys Gln Met Ala Val Lys Lys
1               5                   10                  15

Tyr Leu
```

<210> SEQ ID NO 80
<211> LENGTH: 19
<212> TYPE: PRT
<213> ORGANISM: Homo sapiens

<400> SEQUENCE: 80

Phe Thr Asp Asn Tyr Thr Arg Leu Arg Lys Gln Met Ala Val Lys Lys
1               5                   10                  15

Tyr Leu Asn

<210> SEQ ID NO 81
<211> LENGTH: 20
<212> TYPE: PRT
<213> ORGANISM: Homo sapiens

<400> SEQUENCE: 81

Phe Thr Asp Asn Tyr Thr Arg Leu Arg Lys Gln Met Ala Val Lys Lys
1               5                   10                  15

Tyr Leu Asn Ser
            20

<210> SEQ ID NO 82
<211> LENGTH: 21
<212> TYPE: PRT
<213> ORGANISM: Homo sapiens

<400> SEQUENCE: 82

Phe Thr Asp Asn Tyr Thr Arg Leu Arg Lys Gln Met Ala Val Lys Lys
1               5                   10                  15

Tyr Leu Asn Ser Ile
            20

<210> SEQ ID NO 83
<211> LENGTH: 22
<212> TYPE: PRT
<213> ORGANISM: Homo sapiens

<400> SEQUENCE: 83

Phe Thr Asp Asn Tyr Thr Arg Leu Arg Lys Gln Met Ala Val Lys Lys
1               5                   10                  15

Tyr Leu Asn Ser Ile Leu
            20

<210> SEQ ID NO 84
<211> LENGTH: 23
<212> TYPE: PRT
<213> ORGANISM: Homo sapiens

<400> SEQUENCE: 84

Phe Thr Asp Asn Tyr Thr Arg Leu Arg Lys Gln Met Ala Val Lys Lys
1               5                   10                  15

Tyr Leu Asn Ser Ile Leu Asn
            20

<210> SEQ ID NO 85
<211> LENGTH: 10
<212> TYPE: PRT
<213> ORGANISM: Homo sapiens

<400> SEQUENCE: 85

Gln Met Ala Val Lys Lys Tyr Leu Asn Ser
1               5                   10

```
<210> SEQ ID NO 86
<211> LENGTH: 11
<212> TYPE: PRT
<213> ORGANISM: Homo sapiens

<400> SEQUENCE: 86

Gln Met Ala Val Lys Lys Tyr Leu Asn Ser Ile
1               5                   10

<210> SEQ ID NO 87
<211> LENGTH: 12
<212> TYPE: PRT
<213> ORGANISM: Homo sapiens

<400> SEQUENCE: 87

Gln Met Ala Val Lys Lys Tyr Leu Asn Ser Ile Leu
1               5                   10

<210> SEQ ID NO 88
<211> LENGTH: 13
<212> TYPE: PRT
<213> ORGANISM: Homo sapiens

<400> SEQUENCE: 88

Gln Met Ala Val Lys Lys Tyr Leu Asn Ser Ile Leu Asn
1               5                   10

<210> SEQ ID NO 89
<211> LENGTH: 14
<212> TYPE: PRT
<213> ORGANISM: Homo sapiens

<400> SEQUENCE: 89

Lys Gln Met Ala Val Lys Lys Tyr Leu Asn Ser Ile Leu Asn
1               5                   10

<210> SEQ ID NO 90
<211> LENGTH: 25
<212> TYPE: PRT
<213> ORGANISM: Homo sapiens

<400> SEQUENCE: 90

Ala Val Phe Thr Asp Asn Tyr Thr Arg Leu Arg Lys Gln Met Ala Val
1               5                   10                  15

Lys Lys Tyr Leu Asn Ser Ile Leu Asn
            20                  25

<210> SEQ ID NO 91
<211> LENGTH: 12
<212> TYPE: PRT
<213> ORGANISM: Homo sapiens

<400> SEQUENCE: 91

His Ser Asp Ala Val Phe Thr Asp Asn Tyr Thr Arg
1               5                   10

<210> SEQ ID NO 92
<211> LENGTH: 19
<212> TYPE: PRT
<213> ORGANISM: Homo sapiens

<400> SEQUENCE: 92

Tyr Thr Arg Leu Arg Lys Gln Met Ala Val Lys Lys Tyr Leu Asn Ser
```

```
<210> SEQ ID NO 93
<211> LENGTH: 9
<212> TYPE: PRT
<213> ORGANISM: Homo sapiens

<400> SEQUENCE: 93

Gln Met Ala Val Lys Lys Tyr Leu Asn
1               5

<210> SEQ ID NO 94
<211> LENGTH: 10
<212> TYPE: PRT
<213> ORGANISM: Homo sapiens

<400> SEQUENCE: 94

Arg Lys Gln Met Ala Val Lys Lys Tyr Leu
1               5                   10
```